US005599811A

United States Patent [19]

Berryman et al.

[11] Patent Number: 5,599,811
[45] Date of Patent: Feb. 4, 1997

[54] BENZOTHIAZINE DIOXIDES AS ENDOTHELIN ANTAGONISTS

[75] Inventors: Kent A. Berryman, Ann Arbor; Amy M. Bunker, Ypsilanti; Annette M. Doherty, Ann Arbor; Jeremy J. Edmunds, Ypsilanti, all of Mich.

[73] Assignee: Warner-Lambert Company, Morris Plains, N.J.

[21] Appl. No.: 393,143

[22] Filed: Feb. 21, 1995

[51] Int. Cl.⁶ .................... A61K 31/54; C07D 279/02
[52] U.S. Cl. .................... 514/226.5; 544/49; 544/33; 514/64; 514/81; 514/224.5
[58] Field of Search .................... 544/49, 33; 514/224.5, 514/226.5, 64, 81

[56] References Cited

U.S. PATENT DOCUMENTS

| 4,533,664 | 8/1985 | Trummlitz et al. | 514/225 |
| 5,389,620 | 2/1995 | Ishikawa et al. | 514/80 |

FOREIGN PATENT DOCUMENTS

| 0436189 | 7/1991 | European Pat. Off. |
| 93/08799 | 5/1993 | WIPO |

OTHER PUBLICATIONS

Iijma et al, Chemical Abstracts vol. 117, entry 69873 (1992).
M. Clozel, et al., *Life Sciences*, 1993, 52:825–834.
H. H.Caner, et al., *Cerebral Vasospasm*, 1993, 217–220.
P. L. Foley, et al., *Neurosurgery*, 1994, 34:1, 108–113.
H. Nirei, et al., *Life Sciences*, 1993, 52:1869–1874.
S. Itoh, et al., *Biochem & Biophy Res Comm*, 1993, 195:2, 969–975.
M. Clozel, et al., *Nature*, 1993, 365:759–761.
J–P. Clozel, et al., *Circulation*, 1993, 88:3, 1222–1227.
T. Watanabe, et al., *Nature*, 1990, 344:114.
K. B. Margulies, et al., *Circulation*, 1990, 82:6, 2226–2230.
V. Kon, et al., *J. Clin Invest*, 1989, 83:1762–1767.
N. Perico, et al., *J. Am Soc Nephrol*, 1990, 1:1, 76–83.
T. Koshi, et al., *Chem Pharm Bull*, 1991, 39:5, 1295–1297.
I. Miyamori, et al., *Clin & Exp Pharm & Physiol*, 1990, 17:691–696.
A. Ohno, *J. of Tokyo Women's Med Coll*, 1991, 61:10.11, 951–959.
A. Lerman, et al., *Circulation*, 1991, 83:5, 1808–1814.
R. J. Rodeheffer, et al., *Am J Hypertension*, 1991, 4:9A–10A.
H. Arai, et al., *Nature*, 1990, 348:730–732.
T. Sakurai, et al., *Nature*, 1990, 348:732–735.
H. Y. Lin, *Proc. Natl Acad Sci, USA*, 1991, 88:3185–3189.
A. Sakamoto, et al., *Biochem & Biophys Res Comm*, 1991, 178:2, 656–663.

K. Hosoda, et al., *FEBS*, 1991, 287:1, 2, 23–26.
R. Takayanagi, et al., *FEBS*, 1991, 282:1, 103–106.
R. L. Panek, et al., *Biochem & Biophys Res Comm*, 1992, 183:2, 566–571.
T. Saeki, et al., *Biochem & Biophys Res Comm*, 1991, 179:1, 286–292.
K. Nakagawa, et al., *Nippon Hifuka Gakkai Zasshi*, 1990, 100:1453–1456.
K. Noguchi, et al., *Am Rev Respir Dis*, 1992, 145:4 part 2, A858.
B. Clark, et al., *Am J Obstet Gynecol*, 1992, 962–968.
J–F. Pittet, et al., *Ann Surg*, 1991, 261–264.
C. R. Gandhi, et al., *J of Bio Chem*, 1990, 265:29, 17432–17435.
A. Collier, et al., *Diabetes Care*, 1992 15:8, 1038–1040.
M. K. Basil, et al., *J Hypertension*, 1992, 10:4, S49.
S–P. Han, et al., *Life Sciences*, 1990, 46:767–775.
R. K. Nikolov, et al., *Drugs of Today*, 1992, 28:5, 303–310.
A. Lerman, et al., *New Eng J of Med*, 1991, 325:14, 997–1001.
K. Kanno, et al., *JAMA*, 1990, 264:22, 2868.
M. R. Zamora, et al., *Lancet*, 1990, 1144–1147.
A. Tahara, et al., *Metabolism*, 1991, 40:12, 1235–1237.
D. J. Stewart, et al, *Annals of Int Med*, 1991, 114:464–469.
M. Yasuda, et al., *Am Heart J*, 1990, 119:4, 801–806.
J. T. Stewart, et al., *Br Heart J*, 1991, 66:7–9.
A. Lopez–Farre, et al., *J of Physiology*, 1991, 444:513–522.
F. Stockenhuber, et al., *Clinical Science*, 1992, 82:255–258.
S. Miura, et al., *Digestion*, 1991, 48:163–172.
F. Masuda, et al., *Am J Physiol*, 1992, 262:G785–G790.
S. Murch, et al., *Lancet*, 1992, 339:381–384.
M. Clozel, et al., *Nature*, 1993, 365:759–761.
J. R. Teerlink, et al., *Circulation*, 1994, 90:5, 2510–2518.
M. Clozel, et al., *Life Sciences*, 1993, 52:825–834.
P. D. Stein, et al., *J of Med Chem*, 1994, 37:3, 329–331.
J. D. Elliott, et al., *J Med Chem*, 1994, 37:1553–1557.
S. A. Douglas, et al., *Circulation Research*, 1994, 75:1, 190–197.
D. P. Brooks, et al., *J of Pharm & Exp Ther*, 1994, 271:2, 769–775.
S. M. Berge, et al., *J of Pharm Sci*, 1977, 66:1, 1–19.
Nemazanyi, A. G., et al., *Chemical Abstracts*, 1992, 117:23, Abstract No. 233955q.

*Primary Examiner*—John M. Ford
*Attorney, Agent, or Firm*—Elizabeth M. Anderson

[57] ABSTRACT

Novel benzothiazine dioxides which are antagonists of endothelin are described, as well as novel intermediates used in their preparation, methods for the preparation, and pharmaceutical compositions of the same, which are useful in treating elevated levels of endothelin, essential renovascular malignant and pulmonary hypertension, cerebral infarction, cerebral ischemia, congestive heart failure, and subarachnoid hemorrhage.

15 Claims, No Drawings

BENZOTHIAZINE DIOXIDES AS ENDOTHELIN ANTAGONISTS

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, essential renovascular malignant and pulmonary hypertension, cerebral infarction and cerebral ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, benign prosthetic hyperplasia, ischemic disease, gastric mucosal damage, hemorrhagic shock, ischemic bowel disease, and diabetes.

Also, the compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

Several studies have been reported with both peptide and non-peptide ET antagonists showing efficacy in various models of subarachnoid hemorrhage (SAH). For example, BQ-123-prevents early cerebral vasospasm following SAH in various rat (Clozel M, et al., *Life Sci.* 1993;52:825) and rabbit (Lee K. S., et al., *Cerebral Vasospasm* 1993:217; and *Neurosurgery* 1994; 34:108) models. FR 139317 significantly inhibited the vasoconstriction of the basilar artery after 7 days in a canine two-hemorrhage model of SAH (Nirei H, et al., *Life Sci.* 1993;52:1869). BQ-485 also significantly inhibited the vasoconstriction of the basilar artery after 7 days in a canine two-hemorrhage model of SAH (Yano, et al., *BioChem Biophys. Res Commun.* 1993; 195:969). Ro 46-2005 (Clozel M, et al., *Nature* 1993;365:759) has been shown to prevent early cerebral vasospasm following SAH in the rat with no significant effect on systemic arterial blood pressure. Treatment with Ro 47-0203=Bosentan (Clozel et al., *Circulation* 1993;88(4) part 2:0907) to rabbits with SAH had a 36±7% reduction of basilar artery cross-sectional area compared to sham rabbits. All of these studies show in vivo efficacy of endothelin antagonists in cerebral vasospasm resulting from SAH.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Endothelin is involved in many human disease states.

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of the infarction in a dose-depending manner (Watanabe T, et al., "Endothelin in Myocardial Infarction," *Nature* (Lond.) 1990;344:114). Thus, ET may be involved in the pathogenesis of congestive heart failure and myocardial ischemia (Margulies K. B., et al., "Increased Endothelin in Experimental Heart Failure," *Circulation* 1990;82:2226).

Studies by Kon and colleagues using anti-ET antibodies in an ischemic kidney model, to deactivate endogenous ET, indicated the peptide's involvement in acute renal ischemic injury (Kon V, et al., "Glomerular Actions of Endothelin In Vivo," *J Clin Invest* 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N, et al., "Endothelin Mediates the Renal Vasoconstriction Induced by Cyclosporine in the Rat," *J Am Soc Nephrol* 1990;1:76).

Others have reported inhibition of ET-1 or ET-2-induced vasoconstriction in rat isolated thoracic aorta using a monoclonal antibody to ET-1 (Koshi T, et al., "Inhibition of Endothelin (ET)-1 and ET-2-Induced Vasoconstriction by Anti-ET-1 Monoclonal Antibody," *Chem Pharm Bull* 1991;39:1295).

Combined administration of ET-1 and ET-1 antibody to rabbits showed significant inhibition of the blood pressure (BP) and renal blood flow responses (Miyamori I, et al., Systemic and Regional Effects of Endothelin in Rabbits: Effects of Endothelin Antibody," *Clin Exp Pharmacol Physiol* 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY) there were no significant changes in these parameters (Ohno A, "Effects of Endothelin-Specific Antibodies and Endothelin in Spontaneously Hypertensive Rats," *J Tokyo Women's Med Coll* 1991;61:951).

In addition, elevated levels of endothelin have been reported in several disease states (see Table I below).

Burnett and co-workers recently demonstrated that exogenous infusion of ET (2.5 ng/kg/M1) to anesthetized dogs, producing a doubling of the circulating concentration, did have biological actions (Lerman A, et al., "Endothelin has Biological Actions at Pathophysiological Concentrations," *Circulation* 1991;83:1808). Thus heart rate and cardiac output decreased in association with increased renal and systemic vascular resistances and antinatriuresis. These studies support a role for endothelin in the regulation of cardiovascular, renal, and endocrine function.

In congestive heart failure in dogs and humans, a significant 2- to 3-fold elevation of circulating ET levels has been reported (Rodeheffer R. J., et al., "Circulating Plasma Endothelin Correlates With the Severity of Congestive Heart Failure in Humans," *Am J Hypertension* 1991;4:9A).

The distribution of the two cloned receptor subtypes, termed $ET_A$ and $ET_B$, have been studied extensively (Arai H, et al., *Nature* 1990;348:730, Sakurai T, et al., *Nature* 1990;348:732). The $ET_A$, or vascular smooth muscle receptor, is widely distributed in cardiovascular tissues and in certain regions of the brain (Lin H. Y., et al., *Proc Natl Acad Sci* 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A, et al., *Biochem Biophys Res Chem* 1991;178:656, Hosoda K, et al., *FEBS Lett* 1991;287:23). The $ET_A$ receptor clearly mediates vasoconstriction and there have been a few reports implicating the $ET_B$ receptor in the initial vasodilatory response to ET (Takayanagi R, et al., *FEBS Lett* 1991;282:103). However, recent data has shown that the $ET_B$ receptor can also mediate vasoconstriction in some tissue beds (Panek R. L., et al., *Biochem Biophys Res Commun* 1992;183(2):566).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1,3,11,15-Ala] and truncated analogs ET[6-21,1,3,11,15-Ala], ET[8-21,11,15-Ala], and N-Acetyl-ET[10-21,11,15-Ala] caused vasorelaxation in isolated, endothelium-intact porcine pulmonary arteries (Saeki T, et al., *Biochem Biophys Res Commun* 1991;179:286). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa K, et al., *Nippon Hifuka Gakkai Zasshi* 1990;100:1453-1456).

The ET receptor antagonist BQ-123 has been shown to block ET-1-induced bronchoconstriction and tracheal smooth muscle contraction in allergic sheep providing evidence for expected efficacy in bronchopulmonary diseases such as asthma (Noguchi, et al., *Am Rev Respir Dis* 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark BA, et al., *Am J Obstet Gynecol* 1992;166:962-968).

Plasma immunoreactive endothelin-1 concentrations are elevated in patients with sepsis and correlate with the degree of illness and depression of cardiac output (Pitterr J, et al., *Ann Surg* 1991;213(3):262).

In addition the ET-1 antagonist BQ-123 has been evaluated in a mouse model of endotoxic shock. This $ET_A$ antagonist significantly increased the survival rate in this model (Toshiaki M, et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry* 1990;265(29):17432). In addition increased levels of plasma ET-1 have been observed in microalbuminuric insulin-dependent diabetes mellitus patients indicating a role for ET in endocrine disorders such as diabetes (Collier A, et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M. K., et al., *J Hypertension* 1992;10(Suppl 4):S49). The endothelins have been shown to be arrhythmogenic, and to have positive chronotropic and inotropic effects, thus ET receptor blockade would be expected to be useful in arrhythmia and other cardiovascular disorders (Han S-P, et al., *Life Sci* 1990;46:767).

The widespread localization of the endothelins and their receptors in the central nervous system and cerebrovascular circulation has been described (Nikolov R. K., et al., *Drugs of Today* 1992;28(5):303–310). Intracerebroventricular administration of ET-1 in rats has been shown to evoke several behavioral effects. These factors strongly suggest a role for the ETs in neurological disorders. The potent vasoconstrictor action of Ets on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A, et al., *New England J Med* 1991;325:997–1001). Increased endothelin immunoreactivity has also been associated with Buerger's disease (Kanno K, et al., *J Amer Med Assoc* 1990;264:2868) and Raynaud's phenomenon (Zamora M. R., et al., *Lancet* 1990;336:1144–1147).

An increase of circulating endothelin levels was observed in patients that underwent percutaneous transluminal coronary angioplasty (PTCA) (Tahara A, et al., *Metab Clin Exp* 1991;40:1235–1237).

Increased plasma levels of endothelin have been measured in rats and humans (Stewart D.J. et al., *Ann Internal Medicine* 1991;114:464-469) with pulmonary hypertension.

Elevated levels of endothelin have also been measured in patients suffering from ischemic heart disease (Yasuda M, et al., *Amer Heart J* 1990;119: 801–806) and either stable or unstable angina (Stewart J. T., et al., *Br Heart J* 1991;66:7–9).

Infusion of an endothelin antibody 1 hour prior to and 1 hour after a 60-minute period of renal ischaemia resulted in changes in renal function versus control. In addition, an increase in glomerular platelet-activating factor was attributed to endothelin (Lopez-Farre A, et al., *J Physiology* 1991;444:513–522). In patients with chronic renal failure as well as in patients on regular hemodialysis treatment, mean plasma endothelin levels were significantly increased (Stockenhuber F, et al., *Clin Sci (Lond)* 1992;82: 255–258).

Local intra-arterial administration of endothelin has been shown to induce small intestinal mucosal damage in rats in a dose-dependent manner (Mirua S, et al., *Digestion* 1991;48:163–172). Furthermore, it has been shown that an anti-ET-1 antibody reduced ethanol-induced vasoconstriction in a concentration-dependent manner (Masuda E, et al., *Am J Physiol* 1992;262:G785–790). Elevated endothelin levels have been observed in patients suffering from Crohn's disease and ulcerative colitis (Murch S. H., et al., *Lancet* 1992;339:381–384).

Recently at the 3rd International Conference on Endothelin, Houston, Tex., February 1993, the nonpeptide endothelin antagonist RO 46-2005 has been reported to be effective in models of acute renal ischemia and subarachnoid hemorrhage in rats (Clozel M, et al., "Pathophysiological role of endothelin revealed by the first orally active endothelin receptor antagonist," *Nature* 1993;365:759). A related benzene sulphonamide, namely Bosentan, has also been demonstrated to be useful in the treatment of congestive heart failure. ("Role of endothelin in the maintenance of blood pressure in conscious rats with chronic heart failure cute effects of Bernd M, Hess P, Maire J-P, Clozel M, Clozel J-P, *Circulation* 1994;90(5):2510–2518). In addition, the $ET_A$ antagonist BQ-123 has been shown to prevent early cerebral vasospasm following subarachnoid hemorrhage (Clozel M, Watanabe H, *Life Sci* 1993;52:825–834).

Most recently an $ET_A$ selective antagonist demonstrated an oral antihypertensive effect (Stein P. D., et al., "The Discovery of Sulfonamide Endothelin Antagonists and the Development of the Orally Active ETA Antagonist 5-(Dimethylamino)-N-(3,4-dimethyl-5-isoxazolyl)-1-naphthalenesulfonamide," *J Med Chem* 1994;37:329–331).

Furthermore, a specific $ET_A/ET_B$ receptor antagonist (see WO93 08799A1 and Elliott J. D., et al., *J Med Chem* 1994;37:1553–7) has demonstrated reduced neointimal formation after angioplasty (Douglas S. A., et al., *Circ Res* 1994;75:190–7).

This specific $ET_A/ET_B$ receptor antagonist, SB 209670, has been demonstrated to be beneficial in ischemia-induced acute renal failure (Brooks D. P., et al., "Nonpeptide endothelin receptor antagonists. III. Effect of SB 209670 and BQ123 on acute renal failure in anesthetized dogs," *J Pharmacol Exp Ther* 94;271(2) :769–975).

U.S. Pat. No. 4,533,664 covers compound of the formula

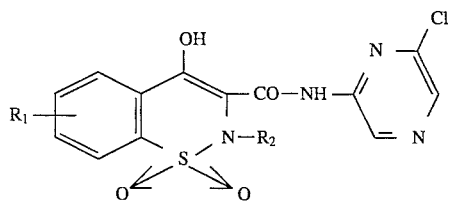

wherein $R_1$ is H, Me, MeO, F, or Cl; and $R_2$ is H, Me, Et, or n-Pr. The compounds are taught as useful as antithrombotic agents.

Copending application U.S. Ser. No. 08/339,381 filed Nov. 14, 1994, covers endothelin antagonists of formula

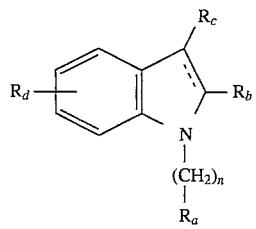

wherein

- - - denotes an optional bond;

n is 0-4;

$R_a$ is hydrogen, alkyl of 1–4 carbon atoms or cycloalkyl, phenyl or naphthyl, in which the phenyl or naphthyl group is substituted by methylenedioxy and further unsubstituted or substituted by one or more substituents selected from the group consisting of halogen, alkyl of 1–6 carbon atoms, OR, $NRR^1$, SR, $NO_2$, $N_3$, COR, $CO_2R$, $CONRR^1$, $SO_2NRR^1$, $SO_2R$, CN, $CF_3$, $CF_2CF_3$, CHO, $OCOCH_3$, $B(OH)_2$, phenyl, $NH(CH_2)_mCO_2R$, $S(CH_2)_mCO_2R$, $O(CH_2)_mCO_2R$, $O(CH_2)_mOR$, $NH(CH_2)_mOR$ and $S(CH_2)_mOR$, in which m is 1, 2 or 3, and R and $R^1$ are each independently hydrogen, alkyl of 1–4 carbon atoms, phenyl or benzyl;

$R_b$ is hydrogen, $CO_2R^2$,

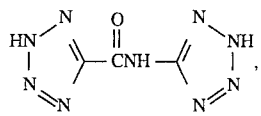

$SO_3R$, $PO_3H$, $B(OH)_2$, $CONR^1R^2$, $SO_2NR^1R^2$, or

—CNHSO$_2R^2$,
‖
O in which $R^1$ is as defined above and $R^2$ is hydrogen, alkyl of 1–6 carbon atoms, $CF_3$, —$CF_2CF_3$, phenyl or benzyl in which phenyl or the phenyl portion of the benzyl group is unsubstituted or substituted by one or more substituents as defined above;

$R_c$ is $S(O)_p$-phenyl, in which p is 0, 1 or 2, and phenyl is unsubstituted or substituted by one or more substituents selected from the group consisting of halogen, OR, $NRR^1$, SR, $NO_2$, $N_3$, COR, $CO_2R$, $CONRR^1$, $SO_2NRR^1$, $SO_2R$, CN, $CF_3$, $CF_2CF_3$, CHO, $OCOCH_3$, $B(OH)_2$, methylenedioxy, $NH(CH_2)_mCO_2R$, $S(CH_2)_mCO_2R$, $O(CH_2)_mCO_2R$, $O(CH_2)_mOR$, $NH(CH_2)_mOR$ and $S(CH_2)_mOR$, in which m, R and $R^1$ are as defined above, and $R_d$ is one to four independent substituents selected from hydrogen, alkyl of 1–7 carbon atoms, alkenyl of 2–7 carbon atoms, alkynyl of 2–7 carbon atoms, cycloalkyl, phenyl, C(O)-phenyl, $X(CH_2)_n$-phenyl, $X$-$(CH_2)_n$-naphthyl, in which X is O, NH or $S(O)_p$, methylenedioxy, OR, $NRR^1$, SR, $NO_2$, $N_3$, COR, $CO_2R$, $CONRR^1$, $SO_2NRR^1$, $SO_2R$, CN, $CF_3$, $CF_2CF_3$, CHO, $OCOCH_3$, $B(OH)_2$, phenyl, $NH(CH_2)_mCO_2R$, $S(CH_2)_mCO_2R$, $O(CH_2)_mCO_2R$, $O(CH_2)_mOR$, $NH(CH_2)_mOR$, $S(CH_2)_mOR$, in which m is 1, 2 or 3 and R and $R^1$ are each independently hydrogen, alkyl of 1–4 carbon atoms, phenyl or benzyl and where n and p are as defined above and phenyl is unsubstituted or substituted as defined above, or a pharmaceutically acceptable acid addition or base salt thereof.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., "Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

SUMMARY OF THE INVENTION

The present invention is compounds of formula

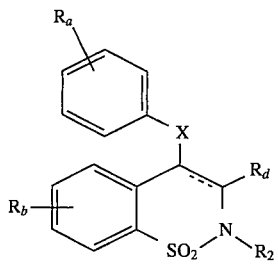

I or a pharmaceutically acceptable acid addition or base salt thereof wherein:

$R_2$ is H,

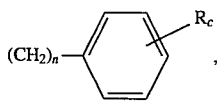

alkyl of from 1 to 7 carbons, $(CH_2)_n$-cycloalkyl of from 3 to 8 carbons;

$R_a$ and $R_c$ are each 1 to 5 substituents and $R_b$ is from to 4 substituents independently selected from:
hydrogen,
alkyl of from 1 to 7 carbons,
alkenyl of from 2 to 7 carbons,
alkynyl of from 2 to 7 carbons,
cycloalkyl of from 3 to 8 carbons,
phenyl,
C(O)-phenyl,
methylenedioxy,
ethylenedioxy,
OR,
$NRR_1$,
$SR_1$,
$NO_2$,
$N_3$,
COR,
$CO_2R$,
Cl,
Br,
F,
I,
$CONRR_1$,
$SO_2NRR_1$,
$SO_2R$,
CN,
$CF_3$,
$CF_2CF_3$,
CHO,
OCOR,
$B(OH)_2$,
$NH(CH_2)_pCO_2R$,
$S(CH_2)_pCO_2R$,
$O(CH_2)_pCO_2R$,
$O(CH_2)_pOR$,
$NH(CH_2)_pOR$,
$S(CH_2)_pOR$, or wherein R and $R_1$ are each independently selected from
hydrogen,
alkyl of from 1 to 6 carbon atoms,
alkenyl of from 2 to 7 carbon atoms,
alkynyl of from 2 to 7 carbon atoms,
cycloalkyl of from 3 to 8 carbon atoms,
phenyl or benzyl wherein the phenyl or benzyl ring is substituted by 1 or more hydrogen, methoxy, and methylenedioxy substituents;

$R_d$ is H, $CO_2R$, $SO_3R$, $PO_3R$, $B(OH)_2$, $CONRR_1$, $SO_2NRR_1$,
$C(O)NHSO_2R_1$,

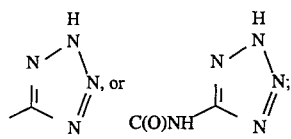

n is an integer of from 0 to 2;

p is an integer of from 1 to 4;

indicates a single or double bond; and

X is $(CH_2)_n$, O, NR, or $S(O)_n$.

Elevated levels of endothelin have been postulated to be involved in a number of pathophysiological states including diseases associated with the cardiovascular system as well as various metabolic and endocrinological disorders. As antagonists of endothelin, the compounds of Formula I are useful in the treatment of essential, renovascular, malignant, and pulmonary hypertension, cerebral infarction, diabetes, cerebral vasospasm, cirrhosis, septic shock, congestive heart failure, endotoxic shock, subarachnoid hemorrhage, arrhythmias, asthma, chronic and acute renal failure, preeclampsia, atherosclerotic disorders including Raynaud's disease and restenosis, angina, cancer, benign prosthetic hyperplasia, ischemic disease, gastric mucosal damage, hemorrhagic shock, and ischemic bowel disease. Particularly, the compounds of Formula I are useful in treating subarachnoid hemorrhage, hypertension, congestive heart failure, and cerebral ischemia and/or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as drowning, pulmonary surgery and cerebral trauma.

A still further embodiment of the present invention is a pharmaceutical composition for administering a therapeutically effective amount of a compound of Formula I in a mixture with a pharmaceutically acceptable carrier in unit dosage form in the treatment methods mentioned above.

Finally, the present invention is directed to novel intermediates used for the production of compounds of Formula I.

DETAILED DESCRIPTION OF THE INVENTION

The compounds of the invention are novel benzothiazine dioxides derivatives of Formula I above.

Preferred compounds of the instant invention are those of Formula I wherein $R_2$ is

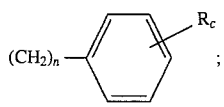

$R_a$ and $R_c$ are each 1 to 5 substituents and $R_b$ is 1 to 4 substituents independently selected from:
hydrogen,
alkyl of from 1 to 3 carbons,
methylenedioxy,
ethylenedioxy,
OH,
methoxy,
propyl oxy,
benzyl oxy,
Cl, Br, F, I,
$O(CH_2)_n$-cycloalkyl of from 3 to 8 carbon atoms,
$O(CH_2)_pCO_2H$,
Rd is $CO_2H$,
n is an integer of from 0 to 1,
p is an integer of from 1 to 4,
- - - indicates a double bond, and
X is $(CH_2)_n$, NH, S, SO, or $SO_2$.

More preferred compounds of the invention are those of Formula I wherein $R_2$ is

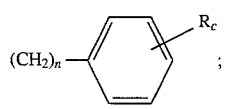

$R_a$ and $R_c$ are each independently 1 to 5 substituents selected from, hydrogen, methoxy, OH, and Cl;
$R_b$ is independently 1 to 5 substituents selected from hydrogen, methoxy, propyloxy, OH, and Cl;
$R_a$, $R_b$, $R_c$ may also independently be 0 to 2 methylenedioxy or ethylenedioxy substituents,
Rd is $CO_2H$,
n is 0 or 1,
- - - indicates a double bond, and
X is $(CH_2)_n$ or S.

Particularly preferred compounds of the instant invention are those of Formula I selected from 4-Benzo[1,3]dioxol-5-yl-2-methyl-1,1-dioxo-1,2-dihydro-1$\lambda^6$-benzo[e][1,2]thiazine-3-carboxylic acid,
4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carboxylic acid,
4-Benzo[1,3]dioxol-5-yl-2-benzyl-1,1-dioxo-1,2-dihydro-1$\lambda^6$-benzo[e][1,2]thiazine-3-carboxylic acid,
4-Benzo[1,3]dioxol-5-yl-2-(4-methoxy-benzyl)-1,1-dioxo-1,2-dihydro-1$\lambda^6$-benzo[e][1,2]thiazine-3-carboxylic acid,
4-Benzo[1,3]dioxol-5-yl-1,1-dioxo-2-(3,4,5-trimethoxybenzyl)-1,2-dihydro-1$\lambda^6$-benzo[e][1,2]thiazine-3-carboxylic acid,
4-Benzo[1,3]dioxol-5-yl-2-(2-carboxymethoxy-4-methoxy-benzyl)-1,1-dioxo-1,2-dihydro-1$\lambda^6$-benzo[e][1,2]thiazine-3-carboxylic acid,
4-Benzo[1,3]dioxol-5-yl-2-(6-chloro-benzo[1,3]dioxol-5-ylmethyl)-1,1-dioxo-1,2-dihydro-1$\lambda^6$-benzo[e][1,2]thiazine-3-carboxylic acid,
4-Benzo[1,3]dioxol-5-yl-2-(7-methoxy-benzo[1,3]dioxol-5-ylmethyl)-1,1-dioxo-1,2-dihydro-1$\lambda^6$-benzo[e][1,2]thiazine-3-carboxylic acid,
2-Benzo[1,3]dioxol-5-ylmethyl-4-(3,4-dimethoxyphenyl)-1,1-dioxo-1,2-dihydro-1$\lambda^6$-benzo[e][1,2]thiazine-3-carboxylic acid,
2-Benzo[1,3]dioxol-5-ylmethyl-1,1-dioxo-4-(3,4,5-trimethoxy-phenyl)-1,2-dihydro-1$\lambda^6$-benzo[e][1,2]thiazine-3-carboxylic acid,
N-(4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carbonyl)benzenesulfonamide,
2-Benzo[1,3]dioxol-5-ylmethyl-4-(3-methoxyphenyl)-1,1-dioxo-1,2-dihydro-1$\lambda^6$-benzo[e][1,2]thiazine-3-carboxylic acid,
4-Benzo[1,3]dioxol-5-yl-2-benzo[1,3]dioxol-5-ylmethyl-6,7-dimethoxy-1,1-dioxo-1,2-dihydro-1$\lambda^6$-benzo[e][1,2]thiazine-3-carboxylic acid,
4-Benzo[1,3]dioxol-5-yl-2-benzo[1,3]dioxol-5-ylmethyl-6-methoxy-1,1-dioxo-1,2-dihydro-1$\lambda^6$-benzo[e][1,2]thiazine-3-carboxylic acid,
8-Benzo[1,3]dioxol-5-yl-6-benzo[1,3]dioxol-5-ylmethyl-5,5-dioxo-5,6-dihydro-1,3-dioxa-5$\lambda^6$-thia-6-aza-cyclopenta[b]naphthalene-7-carboxylic acid,
4-(Benzo[1,3]dioxol-5-ylsulfanyl)-2-methyl-1,1-dioxo-1,2-dihydro-1$\lambda^6$-benzo[e][1,2]thiazine-3-carboxylic acid,
2-Benzo[1,3]dioxol-5-ylmethyl-4-(benzo[1,3]dioxol-5-ylsulfanyl)-1,1-dioxo-1,2-dihydro-1$\lambda^6$-benzo[e][1,2]thiazine-3-carboxylic acid,
4-(Benzo[1,3]dioxol-5-ylsulfanyl)-2-benzyl-1,1-dioxo-1,2-dihydro-1$\lambda^6$-benzo[e][1,2]thiazine-3-carboxylic acid,
4-(Benzo[1,3]dioxol-5-ylsulfanyl)-2-(4-methoxybenzyl)-1,1-dioxo-1,2-dihydro-1$\lambda^6$-benzo[e][1,2]thiazine-3-carboxylic acid,
4-(Benzo[1,3]dioxol-5-ylsulfanyl)-1,1-dioxo-2-(3,4,5-trimethoxy-benzyl)-1,2-dihydro-1$\lambda^6$-benzo[e][1,2]thiazine-3-carboxylic acid,
4-(Benzo[1,3]dioxol-5-ylsulfanyl)-2-(carboxymethoxy-4-methoxy-benzyl)-1,1-dioxo-1,2-dihydro-1$\lambda^6$-benzo[e][1,2]thiazine-3-carboxylic acid,
4-(Benzo[1,3]dioxol-5-ylsulfanyl)-2-(6-chloro-benzo[1,3]dioxol-5-ylmethyl)-1,1-dioxo-1,2-dihydro-1$\lambda^6$-benzo[e][1,2]thiazine-3-carboxylic acid,
4-(Benzo[1,3]dioxol-5-ylsulfanyl)-2-(7-methoxy-benzo[1,3]dioxol-5-ylmethyl)-1,1-dioxo-1,2-dihydro-1$\lambda^6$-benzo[e][1,2]thiazine-3-carboxylic acid,
2-Benzo[1,3]dioxol-5-ylmethyl-4-(3,4-dimethoxy-phenylsulfanyl)-1,1-dioxo-1,2-dihydro-1$\lambda^6$-benzo[e][1,2]thiazine-3-carboxylic acid, 2-Benzo[1,3]dioxol-5-ylmethyl-1,1-dioxo-4-(3,4,5-trimethoxy-phenylsulfanyl)-1,2-dihydro-1$\lambda^6$-benzo[e][1,2]thiazine-3-carboxylic acid, N-(4-Benzo[1,3]dioxol-5-ylsulfanyl-2-benzo[1,3]dioxol-5-ylmethyl-1,1-dioxo-1,2-dihydro- 1$\lambda^6$-benzo[e][1,2]thiazine-3-carbonyl)benzenesulfonamide, 2-Benzo[1,3]dioxol-5-ylmethyl-4-(3-methoxy-phenylsulfanyl)-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-ylsulfanyl)-6,7-dimethoxy-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-ylsulfanyl)-6-methoxy-1,1-dioxo-1,2-dihydro-1$\lambda^6$-benzo[e][1,2]thiazine-3-carboxylic acid, 6-Benzo[1,3]dioxol-5-ylmethyl-8-(benzo[1,3]dioxol-5-ylsulfanyl)-5,5-dioxo-5,6-dihydro-1,3-dioxa -5$\lambda^6$-thia-6-aza-cyclopenta[b]naphthalene-7-carboxylic acid, 4-(Benzo[1,3]dioxol-5-ylsulfanyl)-2-isobutyl-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-ylsulfanyl)-7-methoxy-1,1-dioxo-1,2-dihydro-1$\lambda^6$-benzo[e][1,2]thiazine-3-carboxylic acid, 2-Benzo[1,3]dioxol-5-ylmethyl-4-(2,3-dihydrobenzo[1,4]dioxin-6-ylsulfanyl)-1,1-dioxo-1,2-dihydro-1$\lambda^6$-benzo[e][1,2]thiazine-3-carboxylic acid, 4-(Benzo[1,3]dioxol-5-ylsulfanyl)-2-(2,3-dihydrobenzo[1,4]dioxin-6-ylmethyl)-1,1-dioxo-1,2-dihydro-1$\lambda^6$-benzo[e][1,2]thiazine-3-carboxylic acid, 4-(Benzo[1,3]dioxol-5-ylsulfanyl)-2-cyclohexylmethyl-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfanyl)-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfanyl)-6,7-dimethoxy-1,1-dioxo-1,2-dihydro-1$\lambda^6$-benzo[e][1,2]thiazine-3-carboxylic acid, 2,4-Bis-benzo[1,3]dioxol-5-yl-1,1-dioxo-1,2-dihydro-1$\lambda^6$-benzo[e][1,2]thiazine-3-carboxylic acid, 2,4-Bis-benzo[1,3]dioxol-5-yl-6,7-dimethoxy-1,1-dioxo-1,2-dihydro-1$\lambda^6$-benzo[e][1,2]thiazine-3-carboxylic acid, 4-Benzo[1,3]dioxol-5-yl-2-(2-chloro-benzyl)-1,1-dioxo-1,2-dihydro-1$\lambda^6$-benzo[e][1,2]thiazine-3-carboxylic acid, 2-Benzo[1,3]dioxol-5-ylmethyl-4-(4-chloro-2,6-dimethoxy-phenyl)-1,1-dioxo-1,2-dihydro-1$\lambda^6$-benzo[e][1,2]thiazine-3-carboxylic acid, 4-(Benzo[1,3]dioxol-5-ylsulfanyl)-2-(2-chloro-benzyl)-1,1-dioxo-1,2-dihydro-1$\lambda^6$-benzo[e][1,2]thiazine-3-carboxylic acid, 2-Benzo[1,3]dioxol-5-ylmethyl-4-(4-chloro-2,6-dimethoxy-phenylsulfanyl)-1,1-dioxo-1,2-dihydro-1$\lambda^6$-benzo[e][1,2]thiazine-3-carboxylic acid, 4-(Benzo[1,3]dioxol-5-yl)-2-isobutyl-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-yl)-7-methoxy-1,1-dioxo-1,2-dihydro-1$\lambda^6$-benzo[e][1,2]thiazine-3-carboxylic acid, 2-Benzo[1,3]dioxol-5-ylmethyl-4-(2,3-dihydrobenzo[1,4]dioxin-6-yl)-1,1-dioxo-1,2-dihydro-1$\lambda^6$-benzo[e][1,2]thiazine-3-carboxylic acid, 4-(Benzo[1,3]dioxol-5-yl)-2-(2,3-dihydrobenzo[1,4]dioxin-6-ylmethyl)-1,1-dioxo-1,2-dihydro-1$\lambda^6$-benzo[e][1,2]thiazine-3-carboxylic acid, and 4-(Benzo[1,3]dioxol-5-yl)-2-cyclohexylmethyl-1,1-dioxo-1,2-dihydro-1$\lambda^6$-benzo[e][1,2]thiazine-3-carboxylic acid.

Novel intermediates useful in the preparation of the final products are:

2-Methyl-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-1,1-dioxo-4-(trifluoro-methanesulfonyloxy)-1,2-dihydro-1$\lambda^6$-benzo[e][1,2]thiazine-3-carboxylic acid methyl ester, 2-Benzyl-1,1-dioxo-4-(trifluoro-methanesulfonyloxy)-1,2-dihydro-1$\lambda^6$-benzo[e][1,2]thiazine-3-carboxylic acid methyl ester, 2-(4-Methoxy-benzyl)-1,1-dioxo-4-(trifluoro-methanesulfonyloxy)-1,2-dihydro-1$\lambda^6$-benzo[e][1,2]thiazine-3-carboxylic acid methyl ester, 1,1-Dioxo-4-(trifluoro-methanesulfonyloxy)-2-(3,4,5-trimethoxy-benzyl)-1,2-dihydro-1$\lambda^6$-benzo[e][1,2]thiazine-3-carboxylic acid methyl ester, 2-(2-Ethoxycarbonyl-methoxy-4-methoxy-benzyl)-1,1-dioxo-4-(trifluoro- methanesulfonyloxy)-1,2-dihydro-1$\lambda^6$-benzo[e][1,2]thiazine-3-carboxylic acid methyl ester, 2-(6-Chloro-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, 2-(7-Methoxy-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6,7-dimethoxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6-methoxy-1,1-dioxo-4-(trifluoro-methanesulfonyloxy)-1,2-dihydro-1$\lambda^6$benzo[e][1,2]thiazine-3-carboxylic acid methyl ester, 6-Benzo[1,3]dioxol-5-ylmethyl-5,5-dioxo-8-(trifluoro-methanesulfonyloxy)-5,6-dihydro-1,3-dioxa-5$\lambda^6$-thia-6-aza-cyclopenta[b]naphthalene-7-carboxylic acid methyl ester, 2-Benzo[1,3]dioxol-5-ylmethyl-7-methoxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6-propyloxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-7-propyloxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-7-benzyloxy-6-methoxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6-benzyloxy-7-methoxy-1,1-dioxo-4-(trifluoro-methanesulfonyloxy)-1,2-dihydro-1$\lambda^6$-benzo[e][1,2]thiazine-3-carboxylic acid methyl ester 2-Benzo[1,3]dioxol-5-ylmethyl-6,7,8-trimethoxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-5,6,7,8-tetramethoxy-1,
1-dioxo-4-(trifluoro-methanesulfonyloxy)-1,2-dihy-
dro-1λ$^6$-benzo[e][1,2]thiazine-3-carboxylic acid
methyl ester, 2-Cyclohexylmethyl-1,1-dioxo-4-(trifluoro-methane-
sulfonyloxy)-1,2-dihydro-1λ$^6$-benzo[e][1,2]thiazine-3-
carboxylic acid methyl ester, 2-Cyclopentylmethyl-1,1-dioxo-4-(trifluoro-methane-
sulfonyloxy)-1,2-dihydro-1λ$^6$-benzo[e][1,2]thiazine-3-
carboxylic acid methyl ester, 2-(2-Chloro-benzyl)-1,1-dioxo-4-(trifluoro-methane-
sulfonyloxy)-1,2-dihydro-1λ$^6$-benzo[e][1,2]thiazine-3-
carboxylic acid methyl ester, 2-(2,3-Dihydro-benzo[1,4]dioxin-6-ylmethyl)-1,1-dioxo-
4-(trifluoro-methanesulfonyloxy)-1,2-dihydro-1λ$^6$-
benzo[e][1,2]thiazine-3-carboxylic acid methyl ester, 2-Benzo[1,3]dioxol-5-yl-1,1-dioxo-4-(trifluoro-methane-
sulfonyloxy)-1,2-dihydro-1λ$^6$-benzo[e][1,2]thiazine-3-
carboxylic acid methyl ester, 2-Benzo[1,3]dioxol-5-yl-6,7-dimethoxy-1,1-dioxo-4-(tri-
fluoro-methanesulfonyloxy)-1,2-dihydro-1λ$^6$-benzo[e]
[1,2]thiazine-3-carboxylic acid methyl ester, 2-Benzo[1,3]dioxol-5-yl-6-methoxy-1,1-dioxo-4-(trif-
luoro-methanesulfonyloxy)-1,2-dihydro-1λ$^6$-benzo[e]
[1,2]thiazine-3-carboxylic acid methyl ester, 2-Benzo[1,3]dioxol-5-yl-7-methoxy-1,1-dioxo-4-(trif-
luoro-methanesulfonyloxy)-1,2-dihydro-1λ$^6$-benzo[e]
[1,2]thiazine-3-carboxylic acid methyl ester, 2-Benzo[1,3]dioxol-5-yl-6-propyloxy-1,1-dioxo-4-(trif-
luoro-methanesulfonyloxy)-1,2-dihydro-1λ$^6$-benzo[e]
[1,2]thiazine-3-carboxylic acid methyl ester, 2-Benzo[1,3]dioxol-5-yl-7-propyloxy-1,1-dioxo-4-(trif-
luoro-methanesulfonyloxy)-1,2-dihydro-1λ$^6$-benzo[e]
[1,2]thiazine-3-carboxylic acid methyl ester, 6-Benzo[1,3]dioxol-5-yl-5,5-dioxo-8-(trifluoro-methane-
sulfonyloxy)-5,6-dihydro-1,3-dioxa-5λ$^6$-thia-6-aza-cy-
clopenta[b]naphthalene-7-carboxylic acid methyl ester, 2-Isobutyl-1,1-dioxo-4-(trifluoro-methanesulfonyloxy)-
1,2-dihydro-1λ$^6$-benzo[e][1,2]thiazine-3-carboxylic
acid methyl ester, (5,6,7-Trimethoxy-1,1,3-trioxo-1,3-dihydro-1λ$^6$-benzo
[d]isothiazol-2-yl)-acetic acid methyl ester, 2-Benzo[1,3]dioxol-5-yl-5,6-dimethoxy-1,1-dioxo-1,2-
dihydro-1λ$^6$-benzo[d]isothiazol-3-one, and 2-Benzo[1,3]dioxol-5-yl-1,1-dioxo-1,2-dihydro-1λ$^6$-
benzo[d]isothiazol-3-one.

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl.

The term "alkenyl" means a straight or branched hydrocarbon radical having from 2 to 12 carbon atoms unless otherwise specified and having at least one double bond in the carbon atom chain and includes, for example, 1-ethene, 1-propene, 2-methyl-1-propene, 1-butene, 2-butene, 1-pentene, 2-pentene, 2-methyl-1-butene, 3-methyl-1-butene, 3-methyl-2-butene, 1-hexene, 1-heptene, 1-octene, 1-nonene, 1-decene, 1-undecene, 1-dodecene, and the like.

The term "alkynyl" means a straight or branched hydrocarbon radical having from 2 to 12 carbon atoms unless otherwise specified and having at least one triple bond in the carbon atom chain and includes, for example, 1-ethyne, 1-propyne, 1-butyne, 3-methyl-1-butyne, 1-pentyne, 2-pentyne, 1-hexyne, and the like.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl.

"Halogen" is fluorine, chlorine, bromine or iodine.

Some of the compounds of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see for example, Berge S. M., et al., "Pharmaceutical Salts," *Journal of Pharmaceutical Science* 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example Berge S. M., et al., "Pharmaceutical Salts," *Journal Of Pharmaceutical Science* 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention, possess one or more chiral centers and each center may exist in the R or S configuration. The present invention includes all enantiomeric and epimeric forms as well as the appropriate diastereomeric mixtures thereof.

The compounds of Formula I are valuable antagonists of endothelin. The tests employed indicate that compounds of the invention possess endothelin antagonist activity. Thus, the compounds were tested for their ability to inhibit [$^{125}$I]-ET-1([$^{125}$I]-Endothelin-1) binding in a receptor assay. Selected compounds were also tested for antagonist activity by inhibition of ET-1 stimulated arachidonic acid release and ET-1 stimulated vasoconstriction. The following testing procedures were used (Doherty A. M., et al., "Design of C-Terminal Peptide Antagonists of Endothelin: Structure-Activity Relationships of ET-1 [16-21, D-His[16]]", *Bioorganic and Medicinal Chemistry Letters* 1993;3:497–502).

Radioligand Binding Assays

The following cultured cells were used in binding experiments: rabbit renal artery vascular smooth muscle cells (ERBA-A), Ltk-cells expressing recombinant human $ET_AR$ (HERBA-A), and CHO-K1 cells expressing recombinant human $ET_BR$ (HERBA-B).

Membranes were prepared from cultured cells by lysing cells in cold lysis buffer (5 mM HEPES, 2 mM EDTA, pH 7.4) and homogenizing with a Dounce "A" homogenizer. The homogenate was centrifuged at 30,000× g for 20 minutes at 4° C. Membrane pellets were suspended in cold buffer containing 20 mM Tris, 2 mM EDTA, 200 μM Pefabloc, 10 μM phosphoramidon, 10 μM leupeptin, 1 μM pepstatin at pH 7.4 and frozen at −80° C. until use. Membranes were thawed and homogenized with a Brinkmann Polytron then diluted in tissue buffer containing 20 mM Tris, 2 mM EDTA, 200 μM Pefabloc, and 100 μM bacitracin (pH 7.4). Radioligand and competing ligands were prepared in binding buffer containing 20 mM Tris, 2 mM EDTA, and 0.1% BSA.

Competing binding assays were initiated by combining membranes, [125I]-ET-1 (40 pM) and the competing ligand in a final volume of 250 μL and incubating for 2 hours at 37° C. The assay was terminated by filtration over Whatman GF/B filters which were presoaked with 50 mM Tris, pH 7.4 containing 0.2% BSA and 100 μM bacitracin. Nonspecific binding was defined as binding in the presence of 100 nM ET-1.

IN VITRO INHIBITION OF ET-1 STIMULATED ARACHIDONIC ACID RELEASE (AAR) IN CULTURED RABBIT VASCULAR SMOOTH MUSCLE CELLS($ET_A$) BY THE COMPOUNDS OF THE INVENTION

Antagonist activity is measured by the ability of added compounds to reduce endothelin-stimulated arachidonic acid release in cultured vascular smooth muscle cells. [$^3$H] Arachidonic Acid Loading Media (LM) is DME/F12+0.5% FCS×0.25 mCi/mL [$^3$H] arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 μL of the test compound (1 nM to 1 μM) and 10 μL ET-1 (0.3 nM) and the incubation was extended for 30 minutes. This solution was then collected, 10 mL of scintillation cocktail was added, and the amount of [3H] arachidonic acid was determined in a liquid scintillation counter.

IN VITRO ANTAGONISM OF ET-1 STIMULATED VASOCONSTRICTION (VERA-A) IN THE RABBIT FEMORAL ARTERY ($ET_A$) AND SARAFOTOXIN 6c STIMULATED VASOCONSTRICTION IN THE RABBIT PULMONARY ARTERY ($ET_B$)

Male New Zealand rabbits were killed by cervical dislocation and exsanguination. Femoral and pulmonary arteries were isolated, cleaned of connective tissue, and cut into 4-mm rings. The endothelium was denuded by placing the rings over hypodermic tubing (32 gauge for femoral rings and 28 gauge for pulmonary rings, Small Parts, Inc., Miami, Fla.) and gently rolling them. Denuded rings were mounted in 20 mL organ baths containing Krebs-bicarbonate buffer (composition in mM: NaCl, 118.2; $NaHCO_3$, 24.8; KCl, 4.6; $MgSO_4$ $7H_2O$, 1.2; $KH_2PO_4$, 1.2; $CaCl_2$ 2 $H_2O$ ; Ca-$Na_2$ EDTA, 0.026; dextrose, 10.0), that was maintained at 37° C. and gassed continuously with 5% $CO_2$ in oxygen (pH 7.4). Resting tension was adjusted to 3.0 g for femoral and 4.0 g for pulmonary arteries; the rings were left for 90 minutes to equilibrate. Vascular rings were tested for lack of functional endothelium (i.e., lack of an endothelium-dependent relaxation response to carbachol (1.0 nM) in norepinephrine (0.03 nM) contracted rings. Agonist peptides, ET-1 (femoral), and S6c (pulmonary), were cumulatively added at 10-minute intervals. The ET antagonists were added 30 minutes prior to adding the agonist.

The data in Table I below show the endothelin receptor binding activity of representative compounds of the instant invention.

TABLE I

| Example | HERBAA ($IC_{50}$, μM) | AAR ($IC_{50}$, μM) | VERAA (pA2) | HERBAB ($IC_{50}$, μM) |
| --- | --- | --- | --- | --- |
| 24 | 11 | | | >25 |
| 25 | 1.7 | | | >25 |
| 26 | 0.3 | | | 3.1 |
| 27 | 0.16 | | | 4.6 |
| 29 | 0.17 | | | 4.7 |
| 30 | 1.8 | | | 4.9 |
| 31 | 0.055 | 1.3 | | 0.38 |
| 32 | 0.3 | | | 4.7 |
| 33 | 0.72 | | | 3.6 |
| 35 | 3 | | | >25 |
| 41 | 0.1 | | | 25 |
| 42 | 0.066 | 1.2 | <5.0 | 5.4 |
| 43 | 0.12 | | | 12 |
| 44 | 0.4 | | | 2.3 |
| 45 | 0.2 | | | 12 |
| 46 | 0.51 | | | 22 |
| 48 | 0.23 | | | 8.2 |
| 49 | 0.51 | | | 8.7 |
| 50 | 0.3 | | | 3.5 |

The compounds of Formula I may be prepared by several methods. These methods are illustrated by way of Scheme 1 through 12 and in a detailed manner by way of illustration in the example section of the specification.

Scheme 1 illustrates a procedure used for preparing alkoxy substituted saccharins. The 1,2-benzisothiazol-3(2H)-one (Burri K. F. [4+2] Additions with Isothiazol-3(2H)-one 1,1-dioxide. *Helv Chim Acta* 1990;73:69–80) is alkylated with an alkyl halide, typically propyl iodide, in the presence of a base, typically cesium carbonate in a dipolar aprotic solvent at room temperature. Treatment with acid, typically trifluoroacetic acid at reflux for several days affords the intermediate 6-propyloxysaccharin.

Scheme 2 outlines a procedure for the preparation of appropriately substituted benzothiazine dioxides by way of the corresponding anthranilic acid. Diazotization of the aniline in acid is accomplished typically by treatment with aqueous sodium nitrite. Sulfur dioxide and copper (II) chloride are then addec and the mixture stirred at room temperature for several days in which time the o,o'-dithiodibenzoic acid, methyl ester precipitates (*Meerwein Chem Ber* 1957;90:847). An alternative procedure for the preparation of substituted o,o'-dithiodibenzoic acids involves the treatment of the diazotized anthranilic acid with potassium ethyl xanthate, basic hydrolysis and air oxidation as described in (Katz L, Karger L. S., Scroeder W, Cohen M. Hydrazine Derivatives. I. Benzalthio- and Bisbenzaldithio-Salicylhydrazides. J Orq Chem 1953;18:1380-1402). The disulphide is converted to the sulphonyl chloride by treatment with sulfuryl chloride and potassium nitrate at room temperature (Park Y. J., Shin, H. H., Kim, Y. H. Convenient One-Pot Synthesis of Sulfonyl Chlorides from Thiols Using Sulfuryl Chloride and Metal Nitrate. Chem Lett 1992:1483–1486). Addition of glycine methyl ester and base, typically triethylamine, affords after several hours the corresponding sulphonamide. Treatment of this adduct with sodium methoxide in DMF and acidification with aqueous HCl affords the required benzothiazine dioxide intermediate.

Scheme 3 demonstrates the method employed for the conversion of a saccharin derivative to the corresponding benzothiazine dioxide. Briefly, the saccharin derivative is N-alkylated with methyl bromoacetate in DMF employing sodium hydride as a base. The adduct is rearranged to the corresponding benzothiazine dioxide by treatment with sodium methoxide in DMF at room temperature.

Scheme 4 demonstrates an alternative procedure for preparing the requisite benzothiazine dioxide intermediate. In this situation treatment of the sulphonyl chloride with an appropriately substituted aniline affords the sulphonamide which upon warming affords the N-substituted saccharin. Addition of methyl chloroacetate and sodium hydride results in the isolation of the intermediate benzothiazine dioxide.

Scheme 5 the intermediate benzothiazine dioxide is benzylated typically with (3,4-methylenedioxy)benzyl chloride in DMF in the presence of a base typically sodium hydride. The N-benzylated adduct is treated with trifluoromethanesulphonic anhydride and pyridine in methylene chloride at room temperature for about 1 hour. This intermediate is used directly in the subsequent reactions.

Scheme 6 illustrates the procedure employed for the synthesis of 4-arylsulfanyl benzothiazine dioxides. Typically sodium (3,4-methylenedioxy)phenyl thiolate is added to a solution of the vinyl triflate in DMF. The adduct is isolated by chromatography and saponified with aqueous lithium hydroxide.

Scheme 7 illustrates the procedure employed for the synthesis of 4-aryl benzothiazine dioxides. Typically (3,4-methylenedioxy)phenyl boronic acid is employed in a palladium mediated cross coupling reaction with the corresponding vinyl triflate. The adduct is isolated by chromatography and saponified with aqueous lithium hydroxide.

Scheme 8 depicts the procedure for derivatization the 3-carboxylic acid of the parent benzothiazine dioxide. The acid is activated with a carbodiimide, typically 1-(3-dimethylaminopropyl)-3-ethylcarbodiimide hydrochloride and coupled with a sulphonamide to afford the corresponding carbonyl-arylsulphonamide. Similarly activation with carbonyl diimidazole and addition of aqueous ammonia provides the corresponding amide. This amide is dehydrated with trichloroacetyl chloride and triethylamine to afford the corresponding nitrile. Addition of sodium azide and ammonium chloride to the nitrile in DMF and several hours at elevated temperature, typically 100° C., affords the corresponding tetrazole.

Scheme 9 is an alternate procedure for the preparation of the required benzothiazine dioxides. In this situation the saccharin is N-alkylated by the addition of a base, typically sodium hydride and the addition of the alkylating agent, typically (3,4-methylenedioxy)benzyl chloride. Ring expansion by the addition of chloro methylacetate and NaH, in a dipolar aprotic solvent, such as DMSO, affords the N-alkylated benzothiazine dioxide.

Scheme 10 is an alternate procedure used to prepare substituted saccharins and hence the corresponding benzothiazine dioxide. In this situation the ortho-methyl/sulphonyl chloride product is isolated upon treatment of the parent toluene derivative with chlorosulphonic acid. Oxidation to the corresponding benzoic acid is achieved with aqueous permanganate. The acid chloride and sulphonyl chloride are prepared upon treatment with phosphorus pentachloride. Addition of ammonium hydroxide affords the corresponding saccharin.

Scheme 11 illustrates a procedure employed for the synthesis of substituted 2H-1,2-benzothiazine-3-carbonitrile, 4-hydroxy-, 1,1-dioxide and the subsequent steps required for conversion to the compounds of Formula 1. In this situation the arylsulphonyl chloride is converted to the cyanoacetic sulphonamide by the addition of amino acetonitrile. This sulphonamide is treated with sodium methoxide to afford the required benzothiazine dioxide, upon acidic workup (for an alternative procedure see 1,2-Benzothiazine derivative. ES 508671A1 Foguet Ambros, Rafael, Ortiz Hernandez, Jose Alfonso). This intermediate is benzylated and derivatized to afford the corresponding 4-aryl and 4-arylsulfanyl products by the conditions previously described. The nitrile is then either hydrolyzed to afford the corresponding amide and ultimately the carboxylic acid. The tetrazole is generated by the reaction with tributyltin azide or ammonium chloride and sodium azide in DMF.

Scheme 12 depicts a procedure for preparing benzoisothiazol-3-one dioxides, and hence the corresponding benzothiazine dioxides, by oxidation of the corresponding 1,2-benzoisothiazol-3-ones (see Bambas L. L. "The Chemistry of Heterocyclic Compounds"; Weissburger A. Wiley-Interscience: New York, 1952;4:225–227 and Davis M. *Adv HeteroCycl Chem* 1972;14:43). Reaction of diazotized anthranilic acids with potassium ethyl xanthate followed by hydrolysis, typically with potassium hydroxide, and oxidation, typically with iodine, affords the corresponding 2,2'-dithiosalicylic acid. Addition of thionyl chloride and glycine methyl ester affords the corresponding amide which was cyclized to the 1,2-benzothiazol-3-ones. Oxidation of the 1,2-benzo-isothiazol-3-one to the benzoisothiazol-3-one 1,1-dioxide was achieved with peracetic acid. (Gialdi F. et al., *Farmaco Ed Sci* 1961;16:509–526).

SCHEME 1

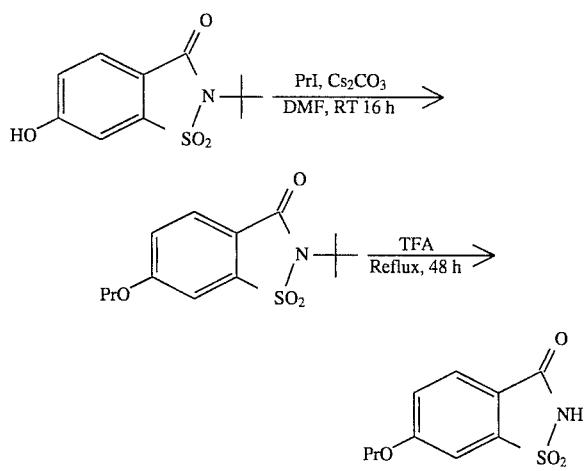

SCHEME 2
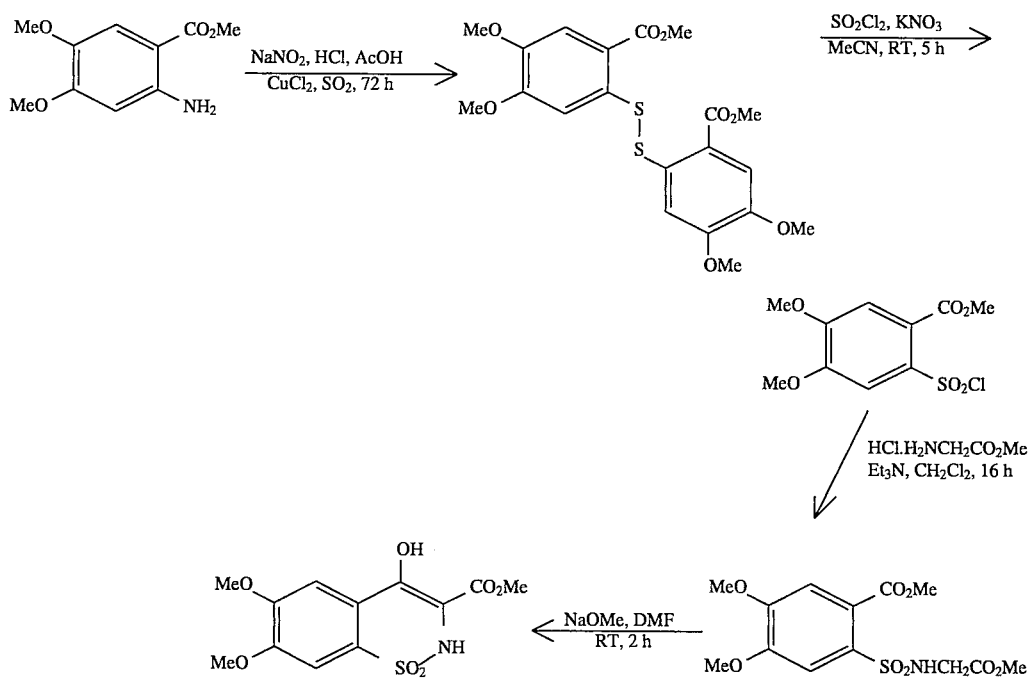
SCHEME 3
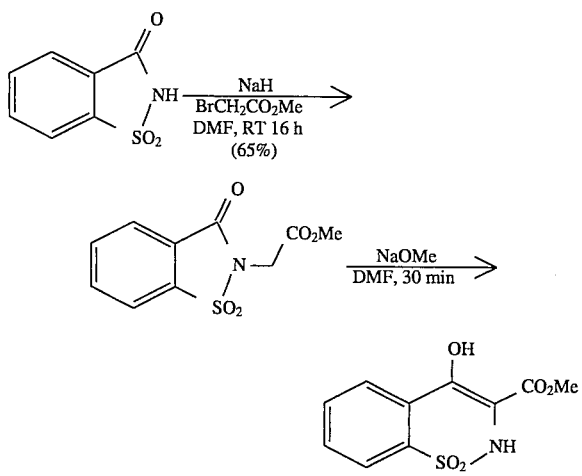
SCHEME 4
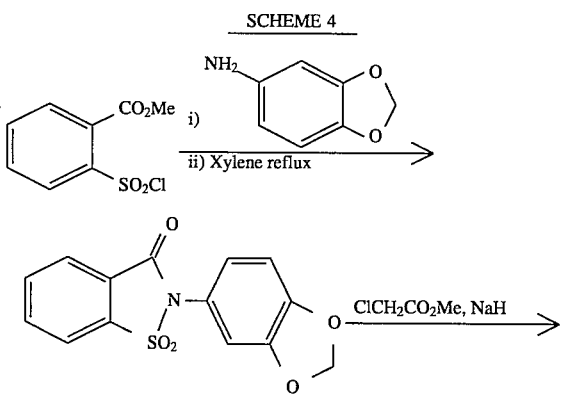
-continued
SCHEME 4
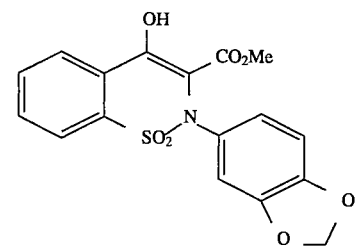
SCHEME 5
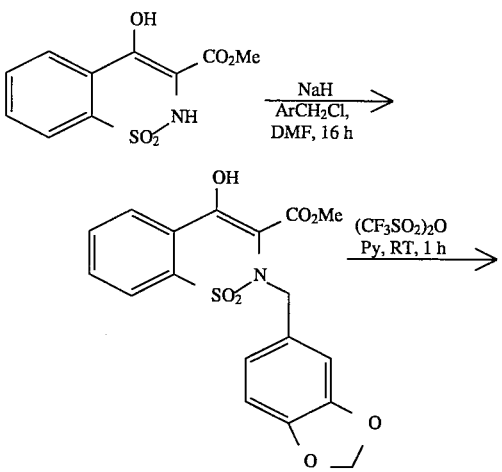

-continued
SCHEME 5
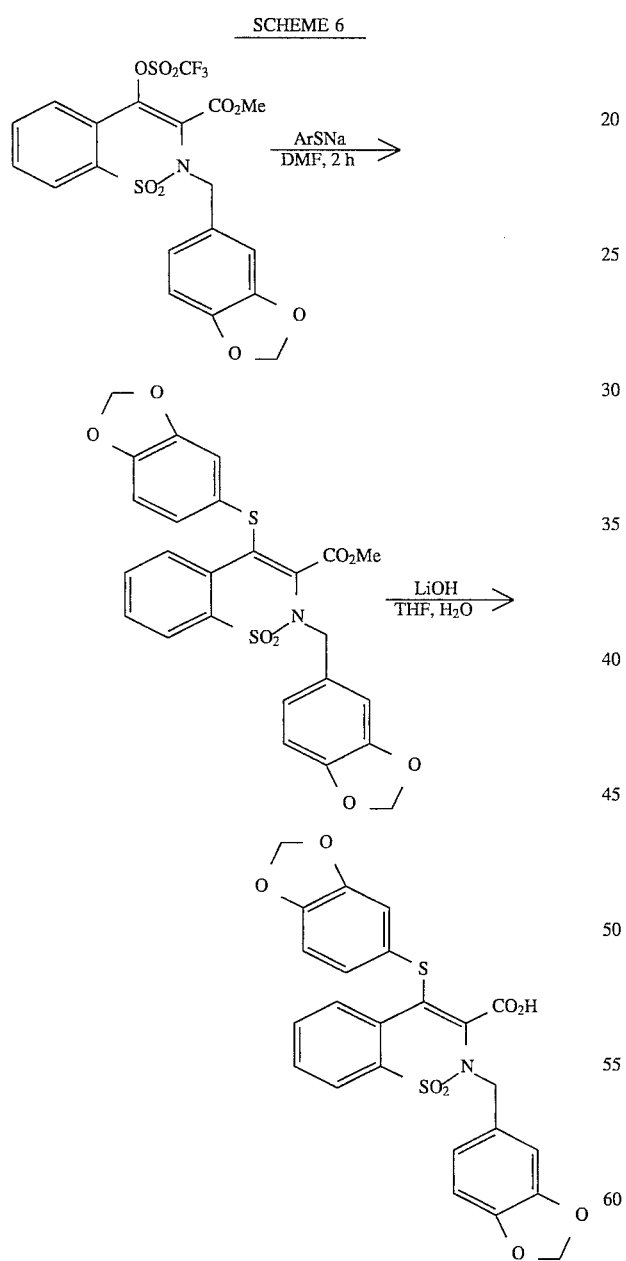
SCHEME 6
SCHEME 7
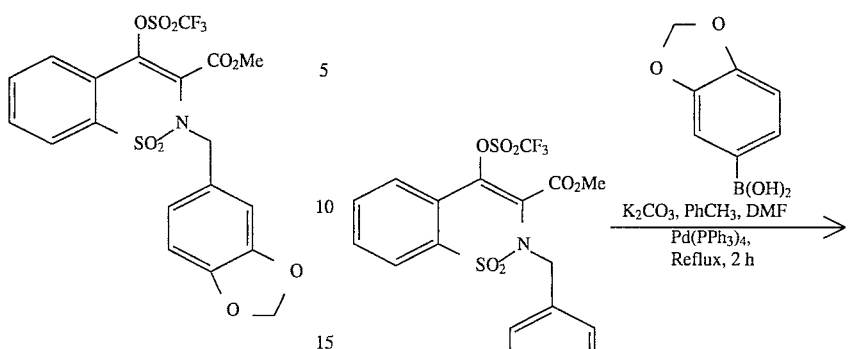
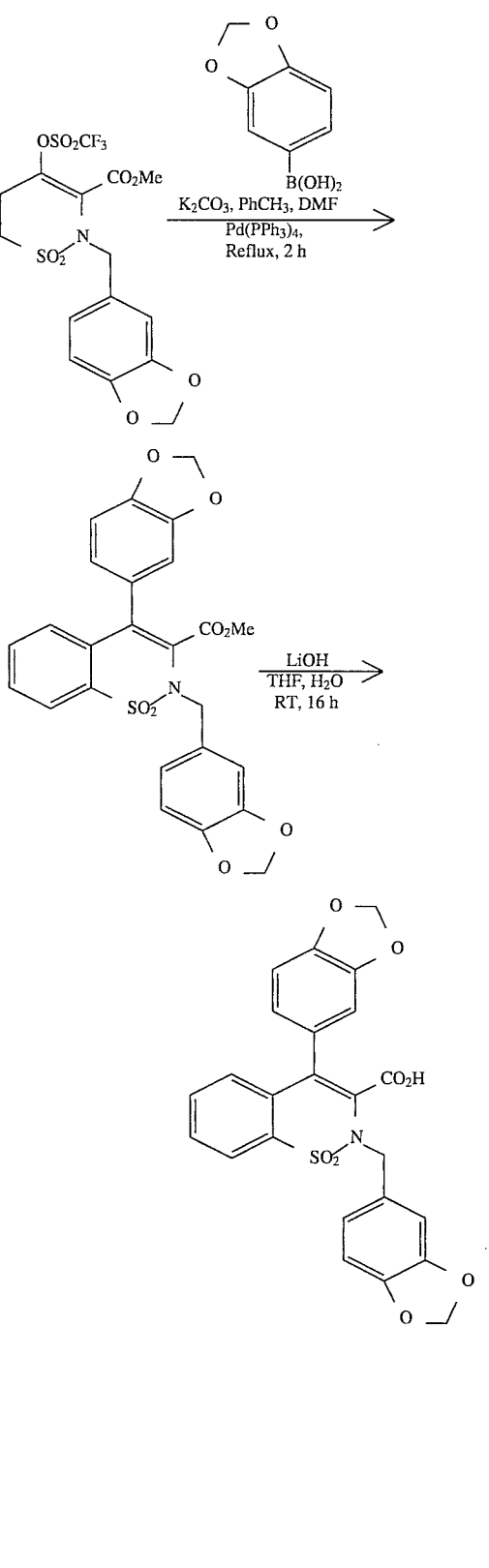

SCHEME 8
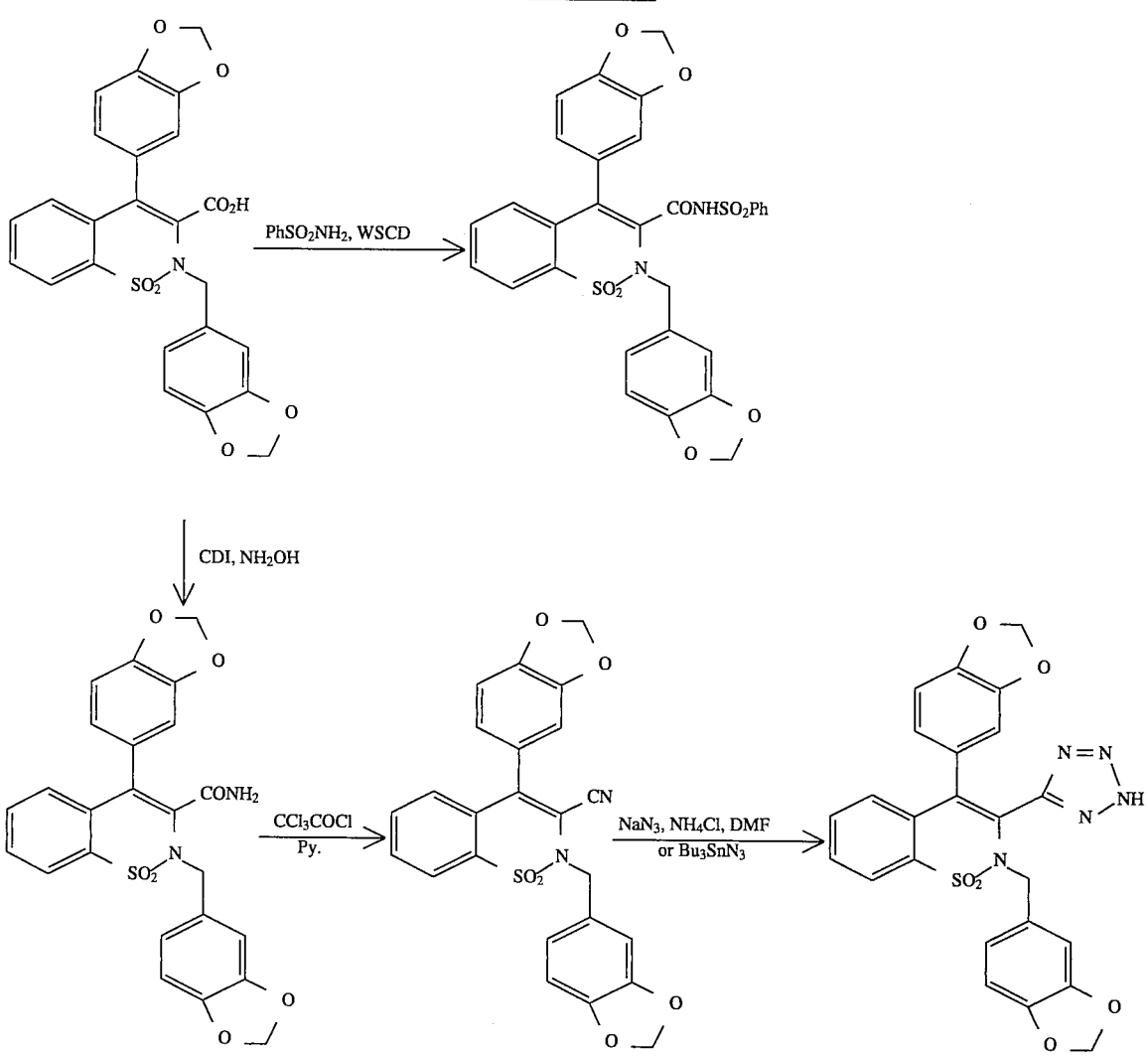
SCHEME 9
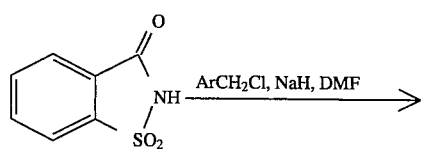

-continued
SCHEME 9
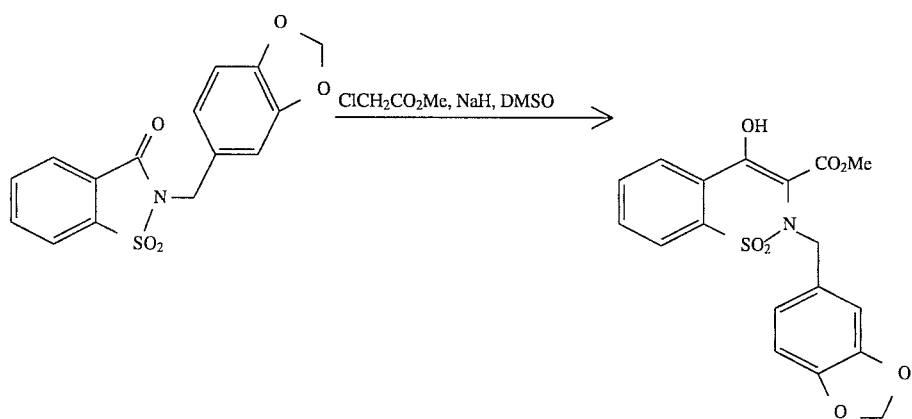
SCHEME 10
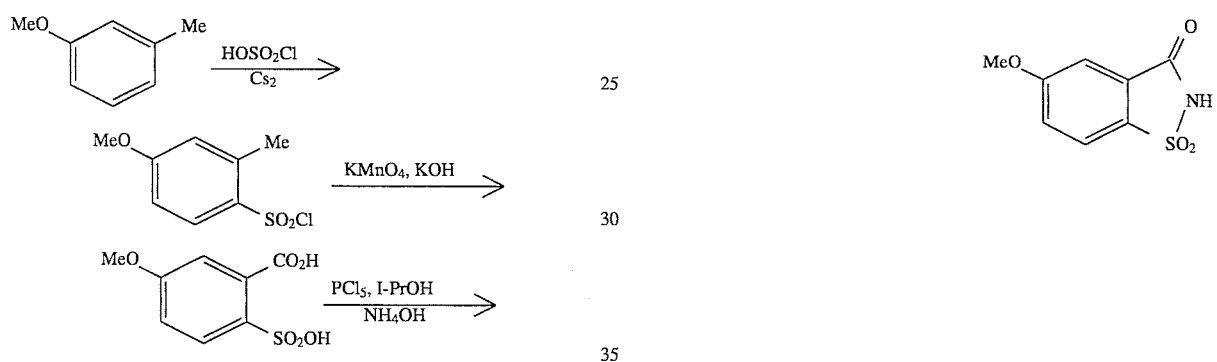
SCHEME 11
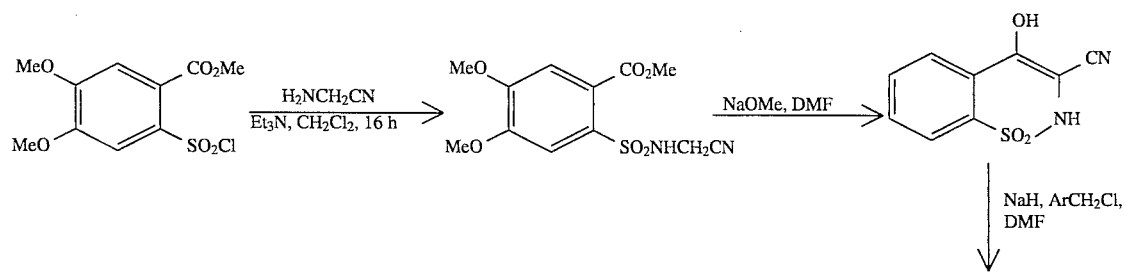

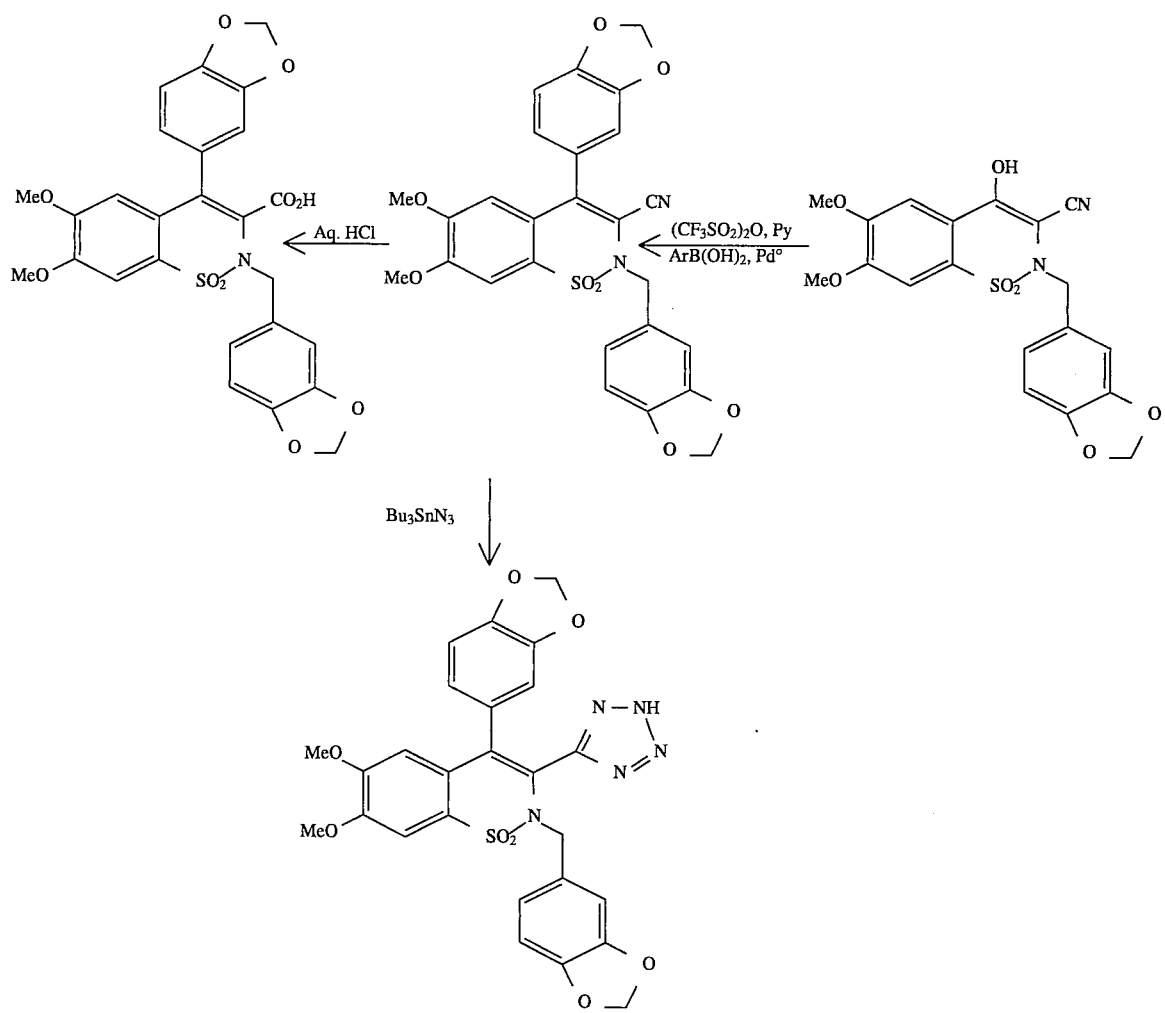
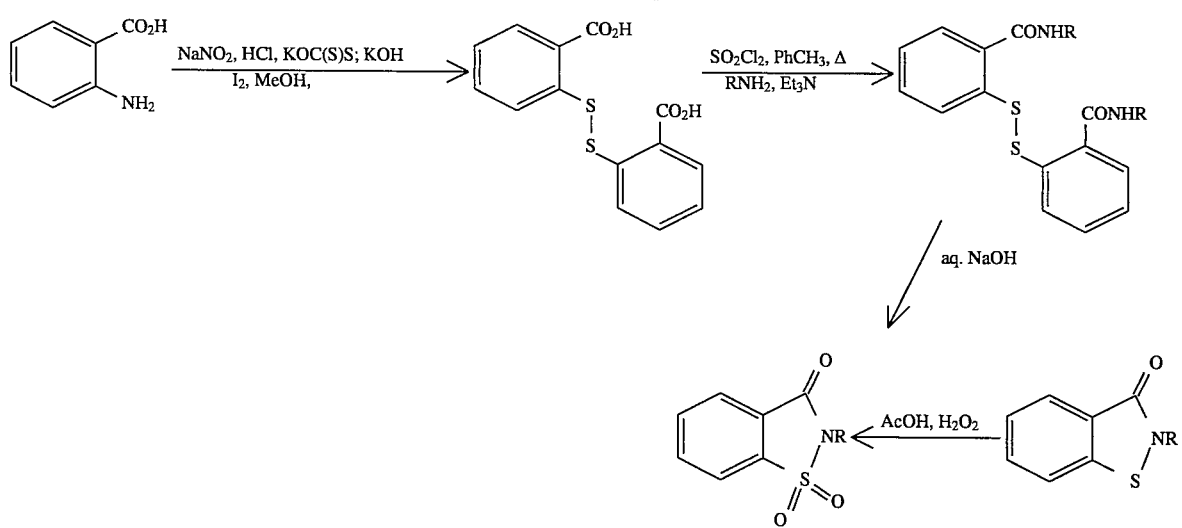

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted from 0.1 mg to 100 mg preferably 0.5 mg to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the preferred methods for preparing the compounds of the invention.

Example/Structure Table
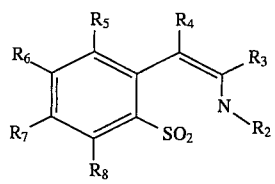
| Example | R$_2$ | R$_3$ | R$_4$ | R$_5$ | R$_6$ | R$_7$ | R$_8$ |
|---|---|---|---|---|---|---|---|
| 24 | 3,4-methylenedioxybenzyl | CO$_2$H | 2,4,6-trimethoxyphenyl | H | H | H | H |
| 25 | Me | CO$_2$H | 3,4-methylenedioxyphenyl | H | H | H | H |
| 26 | 3,4-methylenedioxybenzyl | CO$_2$H | 3,4-methylenedioxyphenyl | H | H | H | H |
| 27 | benzyl | CO$_2$H | 3,4-methylenedioxyphenyl | H | H | H | H |
| 28 | 4-methoxybenzyl | CO$_2$H | 3,4-methylenedioxyphenyl | H | H | H | H |
| 29 | 3,4,5-trimethoxybenzyl | CO$_2$H | 3,4-methylenedioxyphenyl | H | H | H | H |

-continued

Example/Structure Table

[Structure: benzene ring with substituents R5, R6, R7, R8 and side chain with R4, R3, SO2-N(R2) group]

| Example | R2 | R3 | R4 | R5 | R6 | R7 | R8 |
|---------|----|----|----|----|----|----|-----|
| 30 | 2-(OCH2CO2H)-5-(OMe)-benzyl | CO2H | 3,4-methylenedioxyphenyl | H | H | H | H |
| 31 | 2-chloro-4,5-methylenedioxybenzyl | CO2H | 3,4-methylenedioxyphenyl | H | H | H | H |
| 32 | 3,5-dimethoxy-4-oxy-benzyl (3,4-methylenedioxy-5-methoxybenzyl) | CO2H | 3,4-methylenedioxyphenyl | H | H | H | H |
| 33 | 3,4-methylenedioxybenzyl | CO2H | 3,4-dimethoxyphenyl | H | H | H | H |
| 34 | 2-chlorobenzyl | CO2H | 3,4-methylenedioxyphenyl | H | H | H | H |
| 35 | 3,4-methylenedioxybenzyl | CONHSO2Ph | 3,4-methylenedioxyphenyl | H | H | H | H |

-continued
Example/Structure Table
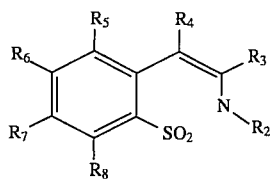
| Example | R₂ | R₃ | R₄ | R₅ | R₆ | R₇ | R₈ |
|---|---|---|---|---|---|---|---|
| 36 | 3,4-methylenedioxybenzyl | $CO_2H$ | 3-MeO-phenyl-S- | H | H | H | H |
| 37 | 3,4-methylenedioxybenzyl | $CO_2H$ | 3,4-methylenedioxyphenyl | H | MeO | MeO | H |
| 38 | 3,4-methylenedioxybenzyl | $CO_2H$ | 3,4-methylenedioxyphenyl | H | MeO | H | H |
| 39 | 3,4-methylenedioxybenzyl | $CO_2H$ | 3,4-methylenedioxyphenyl | H | $-OCH_2O-$ | | H |
| 40 | 3,4-methylenedioxybenzyl | $CO_2Me$ | 3,4-methylenedioxyphenyl-S- | H | H | H | H |

-continued

Example/Structure Table

[Structure: benzene ring with R5, R6, R7, R8 substituents and a vinyl group =C(R4)-C(R3)=N-R2, with SO2 linking the benzene to N]

| Example | R₂ | R₃ | R₄ | R₅ | R₆ | R₇ | R₈ |
|---------|----|----|----|----|----|----|----|
| 41 | Me | CO₂H | [2,3-methylenedioxyphenyl-5-thio] | H | H | H | H |
| 42 | [3,4-methylenedioxybenzyl] | CO₂H | [2,3-methylenedioxyphenyl-5-thio] | H | H | H | H |
| 43 | [phenyl] | CO₂H | [2,3-methylenedioxyphenyl-5-thio] | H | H | H | H |
| 44 | [benzyl] | CO₂H | [2,3-methylenedioxyphenyl-5-thio] | H | H | H | H |
| 45 | [3,4,5-trimethoxybenzyl] | CO₂H | [2,3-methylenedioxyphenyl-5-thio] | H | H | H | H |

-continued
Example/Structure Table
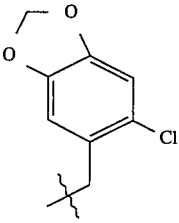
| Example | R₂ | R₃ | R₄ | R₅ | R₆ | R₇ | R₈ |
|---|---|---|---|---|---|---|---|
| 46 | 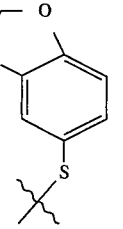 | CO₂H | 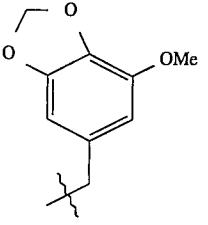 | H | H | H | H |
| 47 | 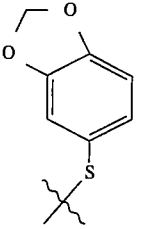 | CO₂H | 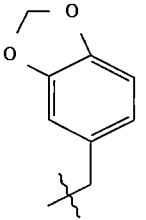 | H | H | H | H |
| 48 | 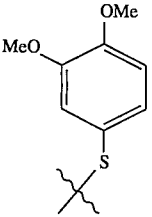 | CO₂H | 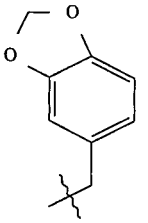 | H | H | H | H |
| 49 | 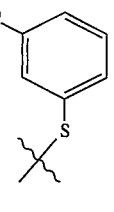 | CO₂H | 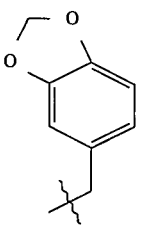 | H | H | H | H |
| 50 | 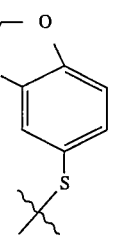 | CO₂H |  | H | MeO | MeO | H |

Example/Structure Table

Structure: benzene ring with substituents R5, R6, R7, R8 on ring, R4 on vinyl, =C(R3)–NH–R2, and SO2 group.

| Example | R₂ | R₃ | R₄ | R₅ | R₆ | R₇ | R₈ |
|---|---|---|---|---|---|---|---|
| 51 | 3,4-methylenedioxybenzyl | CO₂H | (3,4-methylenedioxyphenyl)thiomethyl | H | MeO | H | H |
| 52 | 3,4-methylenedioxybenzyl | CO₂H | (3,4-methylenedioxyphenyl)thiomethyl | H | –OCH₂O– | | H |
| 53 | 2-chlorobenzyl | CO₂H | (3,4-methylenedioxyphenyl)thiomethyl | H | H | H | H |
| 54 | 3,4-methylenedioxybenzyl | CO₂H | (3,4-methylenedioxyphenyl)sulfinylmethyl | H | H | H | H |

EXAMPLE 1

1,2-Benzieothiazole-2(3H)-acetic acid, 3-oxo-, methyl ester, 1,1-dioxide

To a solution of saccharin (40 g, 0.218 mol) in DMF (100 mL) at 0° C. was added sodium hydride (8.73 g, 60%, 0.218 mol). After 15 minutes methyl bromoacetate (20.7 mL, 0.218 mol) was added and the mixture was stirred at room temperature for 18 hours. Diluted with dichloromethane (250 mL) and washed with saturated sodium bicarbonate (2×180 mL), water (100 mL), brine (2×150 mL). Dried organic phase with magnesium sulfate, removed solvent in vacuo, and crystallized product from hot ethanol to give the title compound (36.3 g, 65%).

Analysis calc'd for $C_{10}H_9N_1O_5S_1$: C, 47.06; H, 3.55; N, 5.49; Found: C, 47.02; H, 3.68; N; 5.37. MS (CI) m/e 256. Svoboda J., Palecek J., Dedek V. Phase transfer catalysed N-substitution of 2H-1,2-benzoisothiazolin-3-one 1,1-dioxide. *Collect Czech Chem Commun* 1986;51(6):1304–1310.

EXAMPLE 2

4-Hydroxy-1,1-dioxo-1,2-dihydro-1$\lambda^6$-benzo[e][1,2]thiazine-3-carboxylic acid methyl ester To methanol (100 mL) was added sodium (5.4 g, 0.23 mol) portionwise. Once all the sodium had dissolved the solution was concentrated in vacuo and the final traces of methanol were removed under high vacuum. The sodium methoxide was suspended in dry DMF (65 mL). Dissolved 1,2-Benzisothiazole-2(3H)-acetic acid, 3-oxo-, methyl ester, 1,1-dioxide (20 g, 0.078 mol) in DMF (30 mL), cooled to 0° C., and added the freshly prepared sodium methoxide suspension over 7 minutes. Stirred solution at 0° C. for 30 minutes. Added 1N HCl (430 mL) to reaction via addition funnel, collected and washed precipitate with water. Dried precipitate at 52° C. under vacuum overnight to give the title compound (13.6 g, 68%);

Analysis calc'd for $C_{10}H_9N_1O_5S_1$: C, 47.06; H, 3.55; N, 5.49; Found: C, 47.11; H, 3.67; N; 5.16. MS (CI) m/e 256. Svoboda J., Palecek J., Dedek V. The Synthesis of substituted 2H-1,2-benzothiazines 1,1-dioxides. *Collect Czech Chem Commun* 1986;51(5):1133–1139.

EXAMPLE 3

2-Benzo[1,3]dioxol-5-ylmethyl-4-hydroxy-1,1-dioxo-1,2-dihydro-1$\lambda^6$-benzo[e][1,2]thiazine-3-carboxylic acid methyl ester To 4-hydroxy-1,1-dioxo-1,2-dihydro-1$\lambda^6$-benzo[e][1,2]thiazine-3-carboxylic acid methyl ester (1.48 g, 5.84 mmol) in DMF (10 mL) was added sodium hydride (0.257 g, 60%, 6.4 mmol) and the mixture stirred for 5 minutes. 3,4-methylenedioxybenzyl chloride (2.2 g, 50 wt. % in dichloromethane, 6.4 mmol) was added and the mixture stirred at room temperature for 18 hours. Diluted with ethyl acetate (100 mL), washed with water (2×80 mL), brine (80 mL), dried over magnesium sulfate, removed solvent in vacuo, and crystallized from ethyl acetate/heptane to give the title compound (1.63 g, 72%);

Analysis calc'd for $C_{18}H_{15}N_1O_7S_1$: C, 55.52; H, 3.88; N, 3.60; Found: C, 55.45; H, 3.72; N; 3.49. MS (CI) m/e 389.

EXAMPLE 4

2-Benzo[1,3]dioxol-5-ylmethyl-1,1-dioxo-1,2-dihydro-1$\lambda^6$-benzo[d]isothiazol-3-one To saccharin (5.0 g, 0.0273 mol) in DMF (10 mL) was added NaH (1.15 g, 60% in oil, 0.0288 mol) with ice bath cooling. After stirring for 10 minutes. a solution of 3,4-methylenedioxybenzyl chloride in methylene chloride, 50% by weight, (10 g, 0.0293 mol) was added and the mixture stirred for 16 hours. The mixture was diluted with ethyl acetate (200 mL) containing 10% methylene chloride and washed with 1N HCl (2×100 mL). The organic phase was washed with brine and dried over MgSO$_4$. The mixture was concentrated until crystals were apparent. After standing for 16 hours the product was collected by filtration (4.2 g, 49%);

Analysis calc'd for $C_{15}H_{11}N_1O_5S_1$: C, 56.78; H, 3.49; N, 4.41; Found: C, 56.26; H, 3.50; N, 4.56. MS (CI) m/e 317.

EXAMPLE 5

2-Benzo[1,3]dioxol-5-ylmethyl-4-hydroxy-1,1-dioxo-1,2-dihydro-1$\lambda^6$-benzo[e][1,2]thiazine-3-carboxylic acid methyl ester (Alternative procedure)

To 2-Benzo[1,3]dioxol-5-ylmethyl-1,1-dioxo-1,2-dihydro-1$\lambda^6$-benzo[d]isothiazol-3-one (1.115 g, 3.517 mmol) in DMSO(6 mL) was added methyl 2-chloroacetate (0.61 mL, 6.96 mmol). The mixture was heated to 40° C. and sodium hydride (0.562 g, 60% in oil, 14 mmol) was added slowly over 1 hour. The mixture was maintained at 40° C. for 3 h and then cooled to room temperature and diluted with 1N HCl (100 mL). The mixture was extracted with ethylacetate (2×100 mL) and the organic phase washed with brine and dried over MgSO$_4$. Chromatography, silica gel, eluant CHCl$_3$, and crystallization from methylene chloride/hexane afforded the required product (0.596 g, 44%);

Analysis calc'd for $C_{18}H_{15}N_1O_7S_1$: C, 55.52; H, 3.88; N, 3.60; Found: C, 55.62; H, 3.85; N, 3.52. MS (CI) m/e 389.

EXAMPLE 6

2-tert-Butyl-1,1-dioxo-6-propyloxy-1,2-dihydro-1$\lambda^6$-benzo[d]isothiazo-3-one To a solution of 2-tert-butyl-6-hydroxy-1,1-dioxo-1,2-dihydro-1$\lambda^6$-benzo[d]isothiazol-3-one (0.454 g, 1.78 mmol) in DMF (10 mL) was added cesium carbonate (1.16 g, 3.56 mmol) and the mixture stirred for 10 minutes. 1-iodopropane (0.26 mL, 2.67 mmol) was added and the mixture stirred for 16 hours. Added ethylacetate (100 mL) and water (50 mL). The organic layer was washed with brine and then dried over MgSO$_4$. Concentration in vacuo afforded the required product (0.526 g, 99%). A portion was crystallized from ether/hexane to afford long colorless needles;

Analysis calc'd for $C_{14}H_{19}N_1O_4S_1$: C, 56.55; H, 6.44; N, 4.71; Found: C, 56.72; H, 6.46; N; 4.66. MS (CI) m/e 298.

EXAMPLE 7

1,1-Dioxo-6-propyloxy-1,2-dihydro-1$\lambda^6$-benzo[d]isothiazol-3-one

A solution of 2-tert-butyl-1,1-dioxo-6-propyloxy-1,2-dihydro-1$\lambda^6$-benzo[d]isothiazol-3-one (0.346 g, 1.165 mmol) in trifluoroacetic acid (10 mL) was refluxed for 48 hours. NMR of the reaction mixture revealed quantitative deprotection. The mixture was concentrated in vacuo and crystallized from methylene chloride, methanol and hexane, to afford the required product (0.130 g, 46%);

Analysis calc'd for $C_{10}H_{11}N_1O_4S_1$: C, 49.78; H, 4.60; N, 5.81; Found: C, 49.61; H, 4.49; N; 5.80. MS (CI) m/e 242.

EXAMPLE 8

5-Methoxy-1,1-dioxo-1,2-dihydro-1$\lambda^6$-benzo[d]isothiazol-3-one

Analysis calc'd for $C_8H_7N_1O_4S_1$: C, 45.07; H, 3.31; N, 6.57; Found: C, 45.23; H, 3.31; N; 6.52. MS (CI) m/e 213. Prepared according to Scheme 10 and the method of Haworth R. B., Lapworth A. "Sulphonation of m-cresol and its methyl ether". *J Chem Soc* 1924–1299.

EXAMPLE 9

2-Benzo[1,3]dioxol-5-ylmethyl-5-methoxy-1,1-dioxo-1,2-dihydro-1$\lambda^6$-benzo[d]isothiazol-3-one Prepared according to Example 3;

Analysis calc'd for $C_{16}H_{13}N_1O_6S_1$: C, 55.33; H, 3.77; N, 4.03; Found: C, 55.31; H, 3.81; N; 3.89. MS (CI) m/e 347.

EXAMPLE 10

(5-Methoxy-1,1,3-trioxo-1,3-dihydro-1$\lambda^6$-benzo[d]isothiazol-2-yl)-acetic acid methyl ester Prepared according to Example 1;

Analysis calc'd for $C_{11}H_{11}N_1O_6S_1$: C, 46.31; H, 3.89; N, 4.91; Found: C, 45.93; H, 3.90; N; 4.78. MS (CI) m/e 286.

EXAMPLE 11

Benzoic acid, 2,2'-dithiobis[4,5-dimethoxy-, dimethyl ester

To a suspension of methyl 2-amino-4,5-dimethoxy-benzoate (1.50 g, 7.11 mmol) in acetic acid (10 mL) and conc. HCl (13 mL) at an internal temperature of 1°–3° C. was slowly added a solution of sodium nitrite (0.55 g, 7.97 mmol) in water (5 mL); the solid went into solution upon the final addition of the aqueous sodium nitrite. The solution was stirred for an additional 30 minutes. and then sulphur dioxide was bubbled through the cold solution for 30 minutes. Cupric chloride dihydrate (0.471 g, 2.76 mmol) in water (5 mL) was added and the green mixture allowed to warm to room temperature over 48 hours. Filtration and washing with water (3×100 mL) afforded the required product as a white solid (0.800 g, 49%).

Analysis calc'd for $C_{20}H_{22}O_8S_2$: C, 52.85; H, 4.88; Found: C, 52.64; H, 4.89. MS (CI) m/e 454.

EXAMPLE 12

1,3-Benzodioxole-5-carboxylic acid, 6,6'-dithiobis-, dimethyl ester

Prepared according to the procedure of Example 11 from 6-amino-benzo[1,3]dioxole-5-carboxylic acid methyl ester. Crystallized from methylene chloride/hexane;

Analysis calc'd for $C_{18}H_{14}O_8S_2$: C, 51.18; H, 3.34; Found: C, 51.04; H, 3.33. MS (CI) m/e 422.

EXAMPLE 13

2-Chlorosulfonyl-4,5-dimethoxy-benzoic acid methyl ester

To a suspension of benzoic acid, 2,2' dithiobis 4,5-dimethoxy-, dimethyl ester (0.170 g, 0.374 mmol) in acetonitrile (4 mL) at 0° C. was added potassium nitrate (0.095 g, 0.940 mmol) and then sulfuryl chloride (0.075 mL, 0.934 mmol) dropwise. A yellow solution formed briefly which was replaced rapidly by a heavy precipitate. The mixture was stirred for 1 hour at 0° C. and then for 4 hours at room temperature. Saturated $NaHCO_3$ aq. (10 mL) and ethylacetate (50 mL) were added. The organic fraction was washed with brine and dried over $MgSO_4$. Crystallization from ethylacetate/hexane afforded the required product (0.119 g, 54%);

Analysis calc'd for $C_{10}H_{11}O_6S_1Cl_1$: C, 40.76; H, 3.76; Found: C, 40.79; H, 3.74. MS (CI) m/e 294.

EXAMPLE 14

6-Chlorosulfonyl-benzo[1,3]dioxole-5-carboxylic acid methyl ester

Prepared according to the method of Example 13 from 1,3-benzodioxole-5-carboxylic acid, 6,6'-dithiobis-, dimethyl ester.

Analysis calc'd for $C_9H_7O_6S_1Cl_1$: C, 38.79; H, 2.53. Found: C, 39.19; H, 2.42. MS (CI): m/e 287.

EXAMPLE 15

4,5-Dimethoxy-2-(methoxycarbonylmethyl-sulfamoyl)-benzoic acid methyl ester

To a solution of 2-Chlorosulfonyl-4,5-dimethoxy-benzoic acid methyl ester (0.100 g, 0.339 mmol) in methylene chloride (5 mL) was added triethylamine (0.28 mL, 2.012 mmol) and methyl glycinate.HCl (0.128 g, 1.02 mmol). The mixture was stirred for 2 hours and then diluted with ethyl acetate (50 mL) and 1N HCl (50 mL). The organic fraction was washed with brine and dried over $MgSO_4$. Crystallization from methylene chloride hexane affords the title compound (0.092 g, 78%);

Analysis calc'd for $C_{13}H_{17}N_1O_8S_1$: C, 44.95; H, 4.93; N, 4.03; Found: C, 44.91; H, 4.81; N, 4.09. MS (CI) m/e 347.

EXAMPLE 16

6-(Methoxycarbonylmethyl-sulfamoyl)-benzo[1,3]dioxole-5-carboxylic acid methyl ester Prepared according to the method of Example 15, from 6-Chlorosulfonyl-benzo[1,3]dioxole-5-carboxylic acid methyl ester;

Analysis calc'd for $C_{12}H_{13}N_1O_8S_1$: C, 43.51; H, 3.96; N, 4.23; Found: C, 43.41; H, 3.71; N, 3.99. MS (CI) m/e 331.

EXAMPLE 17

4-Hydroxy-6,7-dimethoxy-1,1-dioxo-1,2-dihydro-1$\lambda^6$-benzo[e][1,2]thiazine-3-carboxylic acid methyl ester To a solution of 4,5-dimethoxy-2-(methoxycarbonylmethyl-sulfamoyl)-benzoic acid methyl ester (0.555 g, 1.60 mmol) in dry DMF (3 mL) was added dry and freshly prepared sodium methoxide (0.345 g, 6.39 mmol). A red colour was generated upon the addition of the sodium methoxide. The mixture was stirred for 45 minutes, and then diluted with 1N HCl (100 mL). The pale yellow solid that precipitated was collected and washed with water (0.341 g, 68%);

Analysis calc'd for $C_{12}H_{13}N_1O_7S_1$: C, 45.71; H, 4.16; N, 4.44; Found: C, 45.67; H, 4.14; N, 4.40. MS (CI) m/e 316.

EXAMPLE 18

8-Hydroxy-5,5-dioxo-5,6-dihydro-1,3-dioxa-5$\lambda^6$-thia-6-aza-cyclopenta[b]naphthalene-7-carboxylic acid methyl ester Prepared according to Example 17 from 6-(methoxycarbonylmethyl-sulfamoyl)-benzo[1,3]dioxole-5-carboxylic acid methyl ester;

Analysis calc'd for $C_{11}H_9N_1O_7S_1$: C, 44.15; H, 3.03; N, 4.68; Found: C, 44.14; H, 2.87; N, 4.24. MS (CI) m/e 299.

EXAMPLE 19

2-Benzo[1,3]dioxol-5-ylmethyl-4-hydroxy-6,7-dimethoxy-1,1-dioxo-1,2-dihydro-1$\lambda^6$-benzo[e][1,2]thiazine-3-carboxylic acid methyl ester Prepared according to the method of Example 3 from 4-hydroxy-6,7-dimethoxy-1,1-dioxo-1,2-dihydro-1$\lambda^6$-benzo[e][1,2]thiazine-3-carboxylic acid methyl ester;

EXAMPLE 20

6-Benzo[1,3]dioxol-5-ylmethyl-8-hydroxy-5,5-dioxo-5,6-dihydro-1,3-dioxa-5$\lambda^6$-thia-6-aza-cyclopenta[b]naphthalene-7-carboxylic acid methyl ester Prepared according to the method of Example 3 from 8-hydroxy-5,5-dioxo-5,6-dihydro-1,3-dioxa-5$\lambda^6$-thia-6-aza-cyclopenta[b]naphthalene-7-carboxylic acid methyl ester;

Analysis calc'd for $C_{19}H_{15}N_1O_9S_1$: C, 52.66; H, 3.49; N, 3.23; Found: C, 52.93; H, 3.81; N, 3.17. MS (CI) m/e 433.

EXAMPLE 21

2-Benzo[1,3]dioxol-5-ylmethyl-4-hydroxy-6-methoxy-1,1-dioxo-1,2-dihydro-1$\lambda^6$-benzo[e][1,2]thiazine-3-carboxylic acid methyl ester Prepared according to the method of Example 3 from 4-hydroxy-6-methoxy-1,1-dioxo-1,2-dihydro-1$\lambda^6$-benzo[e][1,2]thiazine-3-carboxylic acid methyl ester;

Analysis calc'd for $C_{19}H_{17}N_1O_8S_1$: C, 54.41; H, 4.09; N, 3.34; Found: C, 54.22; H, 4.15; N, 3.26. MS (CI) m/e 419.

EXAMPLE 22

2-benzo[1,3]dioxol-5-ylmethyl-1,1-dioxo-4-(trifluoro-methanesulfonyloxy)-1,2-dihydro-1$\lambda^6$-benzo[e][1,2]thiazine-3-carboxylic acid methyl ester A solution of benzo[1,3]dioxol-5-ylmethyl-4-hydroxy-1,1-dioxo-1,2-dihydro-1$\lambda^6$-benzo[e][1,2]thiazine-3-carboxylic acid methyl ester (0.40 g, 1.03 mmol) and pyridine (0.42 mL, 5.14 mmol) in methylene chloride (5 mL) at 0° C. and under $N_2$ was treated with trifluoromethanesulfonic anhydride (0.21 mL, 1.23 mmol) and the reaction mixture stirred at 0° C. for 2 hours. The solution was diluted with ethyl acetate, washed with 1N HCl (2x), brine, dried over magnesium sulfate, and the solvent evaporated. Drying under high vacuum overnight afforded the crude triflate. This was passed through a pad of silica gel eluted with hexane/ethyl acetate 1:1; evaporation and drying under high vacuum afforded the title compound;

Analysis calc'd for $C_{19}H14NO_9S_2F_3$: C, 43.77; H, 2.71; N, 2.69; Found: C, 44.15; H, 2.84; N, 2.59. MS (CI) m/e 521.

EXAMPLE 23

Methyl 2-benzo[1,3]dioxol-5-ylmethyl-1,1-dioxo-4-(3,4,5-trimethoxyphenyl)-1,2-dihydro-1$\lambda^6$-benzo[e][1,2]thiazine-3-carboxylate 2-Benzo[1,3]dioxol-5-ylmethyl-1,1-dioxo-4-(trifluoromethanesulfonyloxy)-1,2-dihydro-1$\lambda^6$-benzo[e][1,2]thiazine-3-carboxylic acid methyl ester was taken up in toluene/DMF (10 mL/2 mL) and treated with (3,4,5-trimethoxy)phenylboronic acid (0.35 g, 1.65 mmol), potassium carbonate (0.23 g, 1.67 mmol), and Pd° (PPh$_3$)$_4$ (0.19 g, 0.16 mmol). The reaction mixture was heated to reflux for 2 hours, cooled to room temperature, diluted with ethyl acetate, washed with sat. aq. NaHCO$_3$, brine, dried over magnesium sulfate, and the solvent evaporated. The residue was purified by silica gel chromatography eluting with hexane/ethyl acetate 1:1. The resulting oil was treated with diethyl ether, the precipitated solid collected, and dried to give the product as an off-white solid;

Analysis calc'd for $C_{27}H_{25}N_1O_9S_1$: C, 59.42; H, 4.41; N, 2.67; Found: C, 59.04; H, 4.42; N, 2.48. MS (CI) m/e 539, mp 182°–183° C.

EXAMPLE 24

2-Benzo[1,3]dioxol-5-ylmethyl-1,1-dioxo-4-(3,4,5-trimethoxyphenyl)-1,2-dihydro-1$\lambda^6$-benzo[e][1,2]thiazine-3-carboxylic acid A solution of methyl 2-benzo[1,3]dioxol-5-ylmethyl-1,1-dioxo-4-(3,4,5-trimethoxyphenyl)-1,2-dihydro-1$\lambda^6$-benzo[e][1,2]thiazine-3-carboxylate (0.28 g, 0.05 mmol) in THF/methanol/water (10 mL/3 mL/3 mL) was treated with lithium hydroxide (0.33 g, 7.78 mmol) and the reaction mixture stirred at room temperature overnight. The solution was diluted with ethyl acetate, washed with 1N HCl, brine, dried over magnesium sulfate, and the solvent evaporated. The foam was crystallized from methylene chloride/isopropyl ether; MS (CI) m/e 525.

EXAMPLE 25

4-Benzo[1,3]dioxol-5-yl-2-methyl-1,1-dioxo-1,2-dihydro-1$\lambda^6$-benzo[e][1,2]thiazine-3-carboxylic acid Prepared according to the method of Example 23, from 2-methyl-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24;

Analysis calc'd for $C_{17}H_{13}NO_6S$: C, 56.82; H, 3.65; N, 3.90; Found: C, 56.68; H, 3.69; N, 3.79. MS (CI) m/e 359, mp 204.0°–205.0° C.

EXAMPLE 26

4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carboxylic acid Prepared according to the method of Example 23, from 2-benzo[1,3]dioxol-5-ylmethyl-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24; MS (CI) m/e 479, mp 229°–230° C.

EXAMPLE 27

4-Benzo[1,3]dioxol-5-yl-2-benzyl-1,1-dioxo-1,2-dihydro-1$\lambda^6$-benzo[e][1,2]thiazine-3-carboxylic acid Prepared according to the method of Example 23, from 2-benzyl-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24; MS (CI) m/e 435.

EXAMPLE 28

4-Benzo[1,3,]dioxol-5-yl-2-(4-methoxy-benzyl)-1,1-dioxo-1,2-dihydro-1$\lambda^6$-benzo[e][1,2]thiazine-3-carboxylic acid Prepared according to the method of Example 23, from 2-(4-methoxy-benzyl)-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24; MS (CI) m/e 465, mp 200°–201° C.

EXAMPLE 29

4-Benzo[1,3]dioxol-5-yl-1,1-dioxo-2-(3,4,5-trimethoxybenzyl)-1,2-dihydro-1$\lambda^6$-benzo[e][1,2]thiazine-3-carboxylic acid Prepared according to the method of Example 23, from 1,1-dioxo-4-(trifluoro-methanesulfonyloxy)-2-(3,4,5-trimethoxy-benzyl)-1,2-dihydro-1$\lambda^6$-benzo[e][1,2]thiazine-3-carboxylic acid methyl ester, and saponification according to the method of Example 24;

Analysis calc'd for $C_{26}H_{23}NO_9S$: C, 59.42; H, 4.41; N, 2.67; Found: C, 56.23; H, 4.38; N, 2.40; H$_2$, 4.42. MS (CI) m/e 525, mp 211.0°–212.0° C.

EXAMPLE 30

4-Benzo[1,3]dioxol-5-yl-2-(2-carboxymethoxy-4-methoxybenzyl)-1,1-dioxo-1,2-dihydro-1$\lambda^6$-benzo[e][1,2]thiazine-3-carboxylic acid Prepared according to the method of Example 23, from 2-(2-ethoxycarbonyl-methoxy-4-methoxy-benzyl)-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24;

Analysis calc'd for $C_{26}H_{21}NO_{10}S$: C, 57.88; H, 3.92; N, 2.60; Found: C, 57.62; H, 3.90; N, 2.54. MS (CI) m/e M-C10H11O4=345, mp 192.0°–192.0° C.

EXAMPLE 31

4-Benzo[1,3]dioxol-5-yl-2-(6-chloro-benzo[1,3]dioxol-5-ylmethyl)-1,1-dioxo-1,2-dihydro-1$\lambda^6$-benzo[e][1,2]thiazine-3-carboxylic acid Prepared according to the method of Example 23, from 2-(6-chloro-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24; MS (CI) m/e 513.

EXAMPLE 32

4-Benzo[1,3]dioxol-5-yl-2-(7-methoxy-benzo[1,3]dioxol-5-ylmethyl)-1,1-dioxo-1,2-dihydro-1$\lambda^6$-benzo[e][1,2]thiazine-3-carboxylic acid Prepared according to the method of Example 23, from 2-(7-methoxy-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24; MS (CI) m/e 509, mp 181°–182° C.

EXAMPLE 33

2-Benzo[1,3]dioxol-5-ylmethyl-4-(3,4-dimethoxy-phenyl)-1,1-dioxo-1,2-dihydro-1$\lambda^6$-benzo[e][1,2]thiazine-3-carboxylic acid Prepared according to the method of Example 23, from 2-(benzo[1,3]dioxol-5-ylmethyl)-1,1-dioxo-4-(trifluoromethanesulfonyloxy)-1,2-dihydro-1$\lambda^6$-benzo[e][1,2]thiazine-3-carboxylic acid methyl ester with 3,4-dimethoxyphenyl boronic acid, and saponification according to the method of Example 24; MS (CI) m/e 495, mp 267°–268° C.

EXAMPLE 34

4-Benzo[2,3]dioxol-5-yl-2-(2-chloro-benzyl)-1,1-dioxo-1,2-dihydro-1$\lambda^6$-benzo[e][1,2]thiazine-3-carboxylic acid Prepared according to the method of Example 24, from 2-(2-chloro-benzyl)-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24;

Analysis calc'd for $C_{23}H_{16}N_1O_6S_1Cl_1$: C, 58.79; H, 3.43; N, 2.84; Found: C, 58.53; H, 3.61; N, 2.84. MS (CI) m/e 470.

EXAMPLE 35

N-(4-Benzo[1,3]dioxo-5-yl-2-benzo[1,3]dioxol-5-ylmethyl-1,1-dioxo-1,2-dihydro-1$\lambda^6$-benzo[e][1,2]thiazine-3-carbonyl)-benzenesulfonamide To a solution of 4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carboxylic acid (0.25 g, 0.56 mmol) in methylene chloride (5 mL) was added benzene sulfonamide (0.10 g, 0.65 mmol), 1-(3-dimethylaminopropyl)-3-ethylcarbodiimide hydrochloride (0.12 g, 0.65 mmol) and dimethylaminopyridine (0.05 9). The mixture was stirred for 3 days and then diluted with ethylacetate (50 mL) and water (20 mL). The organic phase was washed with brine, dried over MgSO$_4$ and evaporated in vacuo. Silica gel chromatography, eluant methylene chloride/ethylacetate afforded the title compound (0.15 g, 46%). MS (CI) m/e 618.

EXAMPLE 36

2-Benzo[1,3]dioxol-5-yl-4-(3-methoxy-phenyl)-1,1-dioxo-1,2-dihydro-1$\lambda^6$-benzo[e][1,2]thiazine-3-carboxylic acid Prepared according to the method of Example 23, from 2-(benzo[1,3]dioxol-5-ylmethyl)-1,1-dioxo-4-(trifluoromethanesulfonyloxy)-1,2-dihydro-1$\lambda^6$-benzo[e][1,2]thiazine-3-carboxylic acid methyl ester with 3-methoxyphenyl boronic acid, and saponification according to the method of Example 24;

Analysis calc'd for $C_7H_7N_7O_7S_7$: C, 61.93; H, 4.11; N, 3.01; Found: C, 61.50; H, 4.40; N, 2.90. MS (CI) m/e 465.

EXAMPLE 37

4-Benzo[1,3]dioxol-5-yl-2-benzo[1,3]dioxol-5-ylmethyl-6,7-dimethoxy-1,1-dioxo-1,2-dihydro-1$\lambda^6$-benzo[e][1,2]thiazine-3-carboxylic acid Prepared according to the method of Example 23, from 2-benzo[1,3]dioxol-5-ylmethyl-6,7-dimethoxy-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24;

Analysis calc'd for $C_{26}H_{21}N_1O_{10}S_1$: C, 57.88; H, 3.92; N, 2.60; Found: C, 57.64; H, 3.94; N, 2.51. MS (CI) m/e 539.

EXAMPLE 38

4-Benzo[1,3]dioxol-5-yl-2-benzo[1,3]dioxol-5-ylmethyl-6-methoxy-1,1-dioxo-1,2-dihydro-1$\lambda^6$-benzo[e][1,2]thiazine-3-carboxylic acid Prepared according to the method of Example 23, from 2-benzo[1,3]dioxol-5-ylmethyl-6-methoxy-1,1-dioxo-4-(trifluoro-methanesulfonyloxy)-1,2-dihydro-1$\lambda^6$-benzo[e][1,2]thiazine-3-carboxylic acid methyl ester, and saponification according to the method of Example 24;

Analysis calc'd for $C_{25}H_{19}N_1O_9S_1$: C, 58.94; H, 3.76; N, 2.75; Found: C, 58.63; H, 3.86; N, 2.64. MS (CI) m/e 509.

EXAMPLE 39

8-Benzo[1,3]dioxol-5-yl-6-benzo[1,3]dioxol-5-ylmethyl-5,5-dioxo-5,6-dihydro-1,3-dioxa-5$\lambda^6$-thia-6-aza-cyclopenta[b]naphthalene-7-carboxylic acid Prepared according to the method of Example 23, from 6-benzo[1,3]dioxol-5-ylmethyl-5,5-dioxo-8-(trifluoro-methanesulfonyloxy)-5,6-dihydro-1,3-dioxa-5$\lambda^6$-thia-6-aza-cyclopenta[b]naphthalene-7-carboxylic acid methyl ester, and saponification according to the method of Example 24;

Analysis calc'd for $C_{25}H_{17}N_1O_{10}S_1$: C, 57.36; H, 3.27; N, 2.68; Found: C, 56.95; H, 3.52; N, 2.53. MS (CI) m/e 523.

EXAMPLE 40

2-Benzo[1,3]dioxol-5-ylmethyl-4-(benzo[1,3]dioxol-5-ylsulfanyl)-1,1-dioxo-1,2-dihydro-1$\lambda^6$-benzo[e][1,2]thiazine-3-carboxylic acid methyl ester To 2-Benzo[1,3]dioxol-5-ylmethyl-4-hydroxy-1,1-dioxo-1,2-dihydro-1$\lambda^6$-benzo[e][1,2]thiazine-3-carboxylic acid methyl ester in dichloromethane (6 mL) and pyridine (0.65 mL, 7.75 mmol) was added trifluoromethanesulfonic anhydride (0.32 mL, 1.71 mmol). This mixture was stirred at room temperature for 30 minutes. Diluted with ethyl acetate (100 mL), washed with 1N HCl (2×50 mL), brine (50 mL), dried with magnesium sulfate and then evaporated in vacuo to afford the crude 2-benzo[1,3]dioxol-5-ylmethyl-6,7-dimethoxy-1,1-dioxo-4-(trifluoro-methanesulfonyloxy)-1,2-dihydro-1$\lambda^6$-benzo[e][1,2]thiazine-3-carboxylic acid methyl ester. A solution of this ester, in DMF (3 mL), was added to sodium 1,3-benzodioxole-5-thiolate (0.31 g, 2.0 mmol) {prepared by dissolving 1,3-benzodioxole-5-thiol (0.31 g, 2.0 mmol) in DMF (3 mL) and stirring with sodium hydride (0.081 g, 2.0 mmol) for 5 minutes} in DMF (3 mL). After stirring at room temperature for 16 hours the mixture was diluted with ethyl acetate (100 mL), washed with 1N NaOH(2×50 mL), brine (50 mL), dried with magnesium sulfate, and evaporated in vacuo. Silica gel column chromatography eluting with 25% ethyl acetate in hexane afforded the title compound as a foam (0.64 g, 79%);

Analysis calc'd for $C_{25}H_{19}N_1O_8S_2$: C, 57.14; H, 3.64; N, 2.67; Found: C, 56.93; H, 3.93; N; 2.51. MS (CI) m/e 525.

EXAMPLE 41

4-(benzo[1,3]dioxol-5-ylsulfanyl)-2-methyl-1,1-dioxo-1,2-dihydro-1$\lambda^6$-benzo[e][1,2]thiazine-3-carboxylic acid Prepared according to the method of Example 40, from 4-hydroxy-2-methyl-1,1-dioxo-1,2-dihydro-1$\lambda^6$-benzo[e][1,2]thiazine-3-carboxylic acid methyl ester and saponified according to the method of Example 42;

Analysis calc'd for $C_{17}H_{13}N_1O_6S_2$: C, 52.17; H, 3.35; N, 3.58; Found: C, 51.94; H, 3.34; N, 3.60. MS (CI) m/e 391.

EXAMPLE 42

2-Benzo[1,3]dioxol-5-ylmethyl-4-(benzo[1,3]dioxol-5-ylsulfanyl)-1,1-dioxo-1,2-dihydro-1$\lambda^6$-benzo[e][1,2]thiazine-3-carboxylic acid To 2-benzo[1,3]dioxol-5-ylmethyl-4-(benzo[1,3]dioxol-5-ylsulfanyl)-1,1-dioxo-1,2-dihydro-1$\lambda^6$-benzo[e][1,2]thiazine-3-carboxylic acid methyl ester (0.467 g, 0.89 mmol) in THF:methanol:water (5 mL:2 mL:2 mL) was added LiOH(0.46 g, 19 mmol). Stirred at room temperature for 5 hours, diluted with water (80 mL) and 50% HCl (10 mL) then extracted with chloroform (3×80 mL). Dried with magnesium sulfate and removed solvent to afford the title compound as a foam (0.4 g, 88%);

Analysis calc'd for $C_{24}H_{17}N_1O_8S_2$: C, 56.35; H, 3.35; N, 2.74; Found: C, 55.78; H, 3.43; N; 2.58. MS (CI) m/e 511.

EXAMPLE 43

4-(benzo[1,3]dioxol-5-ylsulfanyl)-2-benzyl-1,1-dioxo-1,2-dihydro-1$\lambda^6$-benzo[e][1,2]thiazine-3-carboxylic acid Prepared according to the method of Example 40, from 2-benzyl-4-hydroxy-1,1-dioxo-1,2-dihydro-1$\lambda^6$-benzo[e][1,2]thiazine-3-carboxylic acid methyl ester and saponified according to the method of Example 42;

Analysis calc'd for $C_{23}H_{17}N_1O_6S_2$: C, 59.09; H, 3.67; N, 3.00; Found: C, 58.74; H, 3.91; N, 2.68. MS (CI) m/e 467.

EXAMPLE 44

4-(benzo[1,3]dioxol-5-ylsulfanyl)-2-(4-methoxy-benzyl)-1,1-dioxo-1,2-dihydro-1$\lambda^6$-benzo[e][1,2]thiazine-3-carboxylic acid prepared according to the method of Example 40, from 4-hydroxy-2-(4-methoxy-benzyl)-1,1-dioxo-1,2-dihydro-$\lambda^6$-benzo[e][1,2]thiazine-3-carboxylic acid methyl ester and saponified according to the method of Example 42;

Analysis calc'd for $C_{24}H_{19}N_1O_7S_2$: C, 57.94; H, 3.85; N, 2.82; Found: C, 57.97; H, 4.12; N, 2.59. MS (CI) m/e 498.

EXAMPLE 45

4-(benzo[1,3]dioxol-5-ylsulfanyl)-2-(3,4,5-trimethoxy-benzyl)-1,1-dioxo-1,2-dihydro-1$\lambda^6$-benzo[e][1,2]thiazine-3-carboxylic acid Prepared according to the method of Example 40, from 4-hydroxy-1,1-dioxo-2-(3,4,5-trimethoxy-benzyl)-1,2-dihydro-1$\lambda$6-benzo[e][1,2]thiazine-3-carboxylic acid methyl ester and saponified according to the method of Example 42;

Analysis calc'd for $C_{26}H_{23}N_1O_9S_2$: C, 56.01; H, 4.16; N, 2.51; Found: C, 55.97; H, 4.47; N, 2.36. MS (CI) m/e 557.

EXAMPLE 46

4-(Benzo[1,3]dioxol-5-ylsulfanyl)-2-(6-chloro-benzo[1,3]dioxol-5-ylmethyl)-1,1-dioxo-1,2-dihydro-1$\lambda^6$-benzo[e][1,2]thiazine-3-carboxylic acid Prepared according to the method of Example 40, from 2-(6-chloro-benzo[1,3]dioxol-5-ylmethyl)-4-hydroxy-1,1-dioxo-1,2-dihydro-1$\lambda^6$-benzo[e][1,2]thiazine-3-carboxylic acid methyl ester and saponified according to the method of Example 42;

Analysis calc'd for $C_{24}H_{16}N_1O_8S_2Cl_1$: C, 52.80; H, 2.95; N, 2.57; Found: C, 52.91; H, 2.87; N; 2.42. MS (CI) m/e 544, mp 203°–204° C.

EXAMPLE 47

4-(benzo[1,3]dioxol-5-ylsulfanyl)-2-(7-methoxy-benzo[1,3]dioxol-5-ylmethyl)-1,1-dioxo-1,2-dihydro-1$\lambda^6$-benzo[e][1,2]thiazine-3-carboxylic acid Prepared according to the method of Example 40, from 2-(7-methoxy-benzo[1,3]dioxol-5-ylmethyl)-4-hydroxy-1,1-dioxo-1,2-dihydro-1$\lambda^6$-benzo[e][1,2]thiazine-3-carboxylic acid methyl ester and saponified according to the method of Example 42; MS (CI) m/e 541.

EXAMPLE 48

2-Benzo[1,3]dioxol-5-ylmethyl-4-(3,4-dimethoxyphenylsulfanyl)-1,1-dioxo-1,2-dihydro-1$\lambda^6$-benzo[e][1,2]thiazine-3-carboxylic acid Prepared according to the method of Example 40, from 4-hydroxy-2-(3,4-dimethoxy-benzyl)-1,1-dioxo-1,2-dihydro-1$\lambda^6$-benzo[e][1,2]thiazine-3-carboxylic acid methyl ester and saponified according to the method of Example 42;

Analysis calc'd for $C_{25}H_{21}N_1O_8S_2$: C, 56.92; H, 4.01; N, 2.65; Found: C, 57.02; H, 4.10; N; 2.59. MS (CI) m/e 527.

EXAMPLE 49

2-Benzo[1,3]dioxol-5-ylmethyl-4-(3-methoxyphenylsulfanyl)-1,1-dioxo-1,2-dihydro-1$\lambda^6$-benzo[e][1,2]thiazine-3-carboxylic acid Prepared according to the method of Example 40, from 2-Benzo[1,3]dioxol-5-ylmethyl-4-hydroxy-1,1-dioxo-1,2-dihydro-1$\lambda^6$-benzo[e][1,2]thiazine-3-carboxylic acid methyl ester and saponified according to the method of Example 42;

Analysis calc'd for $C_{24}H_{19}N_1O_7S_2$: C, 57.93; H, 3.85; N, 2.82; Found: C, 57.73; H, 4.02; N; 2.63. MS (CI) m/e 497.

EXAMPLE 50

2-Benzo[1,3]dioxol-5-ylmethyl-4-(benzo[1,3]dioxol-5-ylsulfanyl)-6,7-dimethoxy-1,1-dioxo-1,1-dihydro-1$\lambda^6$-benzo[e][1,2]thiazine-3-carboxylic acid Prepared according to the method of Example 40, from 2-Benzo[1,3]dioxol-5-ylmethyl-4-hydroxy-6,7-dimethoxy-1,1-dioxo-1,2-dihydro-1$\lambda^6$-benzo[e][1,2]thiazine-3-carboxylic acid methyl ester and saponified according to the method of Example 42;

Analysis calc'd for $C_{27}H_{23}N_1O_{10}S_2$: C, 54.64; H, 3.70; N, 2.45; Found: C, 54.96; H, 4.08; N, 2.09. MS (CI) m/e 571.

EXAMPLE 51

2-Benzo[1,3]dioxol-5-ylmethyl-4-(benzo[1,3]dioxol-5-ylsulfanyl)-6-methoxy-1,1-dioxo-1,2-dihydro-1$\lambda^6$-benzo[e][1,2]thiazine-3-carboxylic acid Prepared according to the method of Example 40, from 2-benzo[1,3]dioxol-5-ylmethyl-4-hydroxy-6-methoxy-1,1-dioxo-1,2-dihydro-1$\lambda^6$-benzo[e][1,2]thiazine-3-carboxylic acid methyl ester and saponified according to the method of Example 42; MS (CI) m/e 541.

EXAMPLE 52

6-Benzo[1,3]dioxol-5-ylmethyl-8-(benzo[1,3]dioxol-5-ylsulfanyl)-5,5-dioxo-5,6-dihydro-1,3-dioxa-5$\lambda^6$-thia-6-aza-cyclopenta[b]naphthalene-7-carboxylic acid Prepared according to the method of Example 40, from 6-benzo[1,3]dioxol-5-ylmethyl-8-hydroxy-5,5-dioxo-5,6-dihydro-1,3-dioxa-5$\lambda^6$-thia-6-aza-cyclopenta[b]naphthalene-7-carboxylic acid methyl ester and saponified according to the method of Example 42. MS (CI) m/e 555.

EXAMPLE 53

4-(Benzo[1,3]dioxol-5-ylsufanyl)-2-(2-chloro-benzyl)-1,1-dioxo-1,2-dihydro-1$\lambda^6$-benzo[e][1,2]thiazine-3-carboxylic acid Prepared according to the method of Example 40, from 2-(2-chloro-benzyl)-1,1-dioxo-4-(trifluoro-methanesulfonyloxy)-1,2-dihydro-1$\lambda^6$-benzo[e][1,2]thiazine- 3-carboxylic acid methyl ester, and saponification according to the method of Example 42;

Analysis calc'd for $C_{23}H_{16}N_1O_6S_2Cl_1$: C, 55.03; H, 3.21; N, 2.79; Found: C, 54.82; H, 3.85; N, 2.46. MS (CI) m/e 501.

EXAMPLE 54

2-(2-Benzo[1,3]dioxol-5-ylmethyl)-4-(benzo[1,3]dioxol-5-ylsufinyl)-1,1-dioxo-1,2-dihydro-1$\lambda^6$-benzo[e][1,2]thiazine-3-carboxylic acid Addition of meta-chloro perbenzoic acid (1.1 equiv) to a solution of 2-(2-benzo[1,3]dioxol-5-ylmethyl)-4-(benzo[1,3]dioxol-5-ylsufanyl)-1,1-dioxo-1,2-dihydro-1$\lambda^6$-benzo[e][1,2]thiazine-3-carboxylic acid methyl ester in methylene chloride and stirring for 10 minutes affords, upon workup, 2-(2-benzo[1,3]dioxol-5-ylmethyl)-4-(benzo[1,3]dioxol-5- ylsufinyl)-1,1-dioxo-1,2-dihydro-1λ⁶-benzo[e][1,2]thiazine-3-carboxylic acid methyl ester, which was saponified according to the procedure of Example 42;

Analysis calc'd for $C_{24}H_{17}N_1O_9S_2$: C, 54.64; H, 3.25; N, 2.66; Found: C, 54.75; H, 3.38; N, 2.61. MS (CI) m/e 527.

EXAMPLE 55

2-Benzo[1,3]dioxol-5-yl-1,1-dioxo-1,2-dihydro-1λ⁶-benzo-[d][isothiazol-3-one To a solution of 3,4-methylenedioxyaniline (9.5 g, 36.5 mmol) and pyridine (3.53 mL, 43.6 mmol) in chloroform (20 mL) at 0° C. was added 90% methyl 2-(chlorosulfonyl)benzoate (9.5 g, 36.5 mmol) in portions over 45 minutes. Stirred at room temperature for 3 days. Diluted with ethyl acetate and washed with 1N HCl. After drying over MgSO₄ the crude sulphonamide was dissolved in xylenes (100 mL) and treated with pyridine (0.61 mL, 7.64 mmol) and DMAP (0.93 g, 7.64 mmol) and heated to reflux for 18 hours. The reaction mixture was evaporated in vacuo and triturated with 1N HCl. The solid was collected, washed with water, and dried to afford the title compound;

Analysis calc'd for $C_{14}H_9N_1O_5S$: C, 55.44; H, 2.99; N, 4.62; Found: C, 55.43; H, 3.08; N, 4.70. MS (CI) m/e 303.

EXAMPLE 56

2-Benzo[1,3]dioxol-5-yl-4-hydroxy-1,1-dioxo-1,2-dihydro-1λ⁶-benzo[e][1,2]thiazine-3-carboxylic acid methyl ester To a solution of 2-benzo[1,3]dioxol-5-yl-1,1-dioxo-1,2-dihydro-1λ⁶-benzo[d][isothiazol-3-one (2 g, 6.59 mmol) in DMSO (11 mL) was added methyl 2-chloroacetate (1.16 mL, 13.2 mmol) and the mixture heated to 40° C. To this was added 60% NaH (1.05 g, 26.4 mmol) in portions over 1 hour. The reaction was maintained at 40° C. for a further 3 hours, acidified with 1N HCl, extracted into ethylacetate, washed with brine and dried over MgSO₄. Chromatography afforded the required product;

Analysis calc'd for $C_{17}H_{13}N_1O_7S$: C, 54.40; H, 3.49; N, 3.73; Found: C, 54.11; H, 3.66; N, 3.60. MS (CI) m/e 375.

We claim:

1. A compound of formula

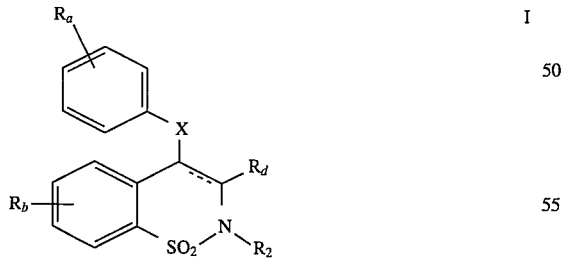

I or a pharmaceutically acceptable acid addition or base salt thereof wherein:

$R_2$ is

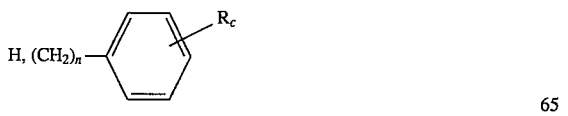

or $(CH_2)_n$-cycloalkyl of from 3 to 8 carbons;

$R_a$ and $R_c$ are each 1 to 5 substituents and $R_b$ is 1 to 4 substituents independently selected from:
hydrogen,
alkyl of from 1 to 7 carbons,
alkenyl of from 2 to 7 carbons,
alkynyl of from 2 to 7 carbons,
cycloalkyl of from 3 to 8 carbons,
phenyl,
C(O)-phenyl,
methylenedioxy,
ethylenedioxy,
OR,
$NRR_1$,
$SR_1$,
$NO_2$,
$N_3$,
COR,
Cl,
Br,
F,
I,
$CO_2R$,
$CONRR_1$,
$SO_2NRR_1$,
$SO_2R$,
CN,
$CF_3$,
$CF_2CF_3$,
CHO,
OCOR,
$B(OH)_2$,
$NH(CH_2)_pCO_2R$,
$S(CH_2)_pCO_2R$,
$O(CH_2)_pCO_2R$,
$O(CH_2)_pOR$,
$NH(CH_2)_pOR$, and
$S(CH_2)_pOR$;

wherein R and $R_1$ are each independently selected from
hydrogen,
alkyl of from 1 to 6 carbon atoms,
alkenyl of from 2 to 7 carbon atoms,
alkynyl of from 2 to 7 carbon atoms,
cycloalkyl of from 3 to 8 carbon atoms,
phenyl or benzyl wherein the phenyl or benzyl ring is substituted by 1 or more H, methoxy, and methylenedioxy substituents;

$R_d$ is H, $CO_2R$, $CO_3R$, $PO_4H$, $B(OH)_2$, $CONRR_1$, $SO_2NRR_1$,

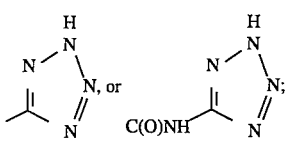

n is an integer of from 0 to 2;
p is an integer of from 1 to 4;
- - - indicates a single or double bond; and
X is $(CH_2)_n$, O, MR, or $S(O)_n$.

2. A compound of formula

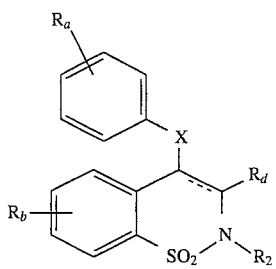

or a pharmaceutically acceptable acid addition or base salt thereof wherein $R_2$ is

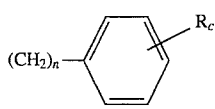

or $(CH_2)_n$-cycloalkyl of from 5 to 7 carbons;

$R_a$ and $R_c$ are each 1 to 5 substituents and $R_b$ is 1 to 4 substituents selected from:
hydrogen,
alkyl of from 1 to 3 carbons,
methylenedioxy,
ethylenedioxy,
OH,
methoxy,
propyloxy,
benzyloxy,
Cl, Br, F, I
$O(CH_2)_n$-cycloalkyl of from 3 to 8 carbon atoms,
$O(CH_2)_pCO_2H$, Rd is $CO_2H$ n is an integer of from 0 to 1, p is an integer of from 1 to 4,

- - - indicates a double bond, and

X is $(CH_2)_n$, NH, S, SO, or $SO_2$.

3. A compound according to claim 2 wherein $R_2$ is

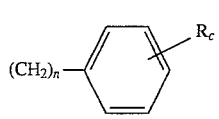

or $(CH_2)_n$-cycloalkyl of from 5 to 7 carbons;

$R_a$ and $R_c$ are each independently 1 to 5 substituents selected from, hydrogen, methoxy, OH, and Cl;

$R_b$ is independently 1 to 5 substituents selected from hydrogen, methoxy, propyloxy, OH, and Cl;

$R_a, R_b, R_c$ may also independently be 0 to 2 methylenedioxy or ethylenedioxy substituents, $R_d$ is $CO_2H$, n is 0 or 1,

- - - indicates a double bond, and

X is $(CH_2)_n$ or S.

4. A compound selected from

4-Benzo[1,3]dioxol-5-yl-2-methyl-1,1-dioxo-1,2-dihydro-1$\lambda^6$-benzo[e][1,2]thiazine-3-carboxylic acid, 4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carboxylic acid, 4-Benzo[1,3]dioxol-5-yl-2-benzyl-1,1-dioxo-1,2-dihydro-1$\lambda^6$-benzo[e][1,2]thiazine-3-carboxylic acid, 4-Benzo[1,3]dioxol-5-yl-2-(4-methoxy-benzyl)-1,1-dioxo-1,2-dihydro-1$\lambda^6$-benzo[e][1,2]thiazine-3-carboxylic acid, 4-Benzo[1,3]dioxol-5-yl-1,1-dioxo-2-(3,4,5-trimethoxy-benzyl)-1,2-dihydro-1$\lambda^6$-benzo[e][1,2]thiazine-3-carboxylic acid, 4-Benzo[1,3]dioxol-5-yl-2-(2-carboxymethoxy-4-methoxy-benzyl)-1,1-dioxo-1,2-dihydro-1$\lambda^6$-benzo[e][1,2]thiazine-3-carboxylic acid, 4-Benzo[1,3]dioxol-5-yl-2-(6-chloro-benzo[1,3]dioxol-5-ylmethyl)-1,1-dioxo-1,2-dihydro-1$\lambda^6$-benzo[e][1,2]thiazine-3-carboxylic acid, 4-Benzo[1,3]dioxol-5-yl-2-(7-methoxy-benzo[1,3]dioxol-5-ylmethyl)-1,1-dioxo-1,2-dihydro-1$\lambda^6$-benzo[e][1,2]thiazine-3-carboxylic acid, 2-Benzo[1,3]dioxol-5-ylmethyl-4-(3,4-dimethoxy-phenyl)-1,1-dioxo-1,2-dihydro-1$\lambda^6$-benzo[e][1,2]thiazine-3-carboxylic acid, 2-Benzo[1,3]dioxol-5-ylmethyl-1,1-dioxo-4-(3,4,5-trimethoxy-phenyl)-1,2-dihydro-1$\lambda^6$-benzo[e][1,2]thiazine-3-carboxylic acid, N-(4-Benzo[1,3]dioxol-5-yl-2-benzo[1,3]dioxol-5-ylmethyl-1,1-dioxo-1,2-dihydro-1$\lambda^6$-benzo[e][1,2]thiazine-3-carbonyl)benzenesulfonamide, 2-Benzo[1,3]dioxol-5-yl-4-(3-methoxy-phenyl)-1,1-dioxo-1,2-dihydro-1$\lambda^6$-benzo[e][1,2]thiazine-3-carboxylic acid., 4-Benzo[1,3]dioxol-5-yl-2-benzo[1,3]dioxol-5-ylmethyl-6,7-dimethoxy-1,1-dioxo-1,2-dihydro-1$\lambda^6$-benzo[e][1,2]thiazine-3-carboxylic acid., 4-Benzo[1,3]dioxol-5-yl-2-benzo[1,3]dioxol-5-ylmethyl-6-methoxy-1,1-dioxo-1,2-dihydro-1$\lambda^6$-benzo[e][1,2]thiazine-3-carboxylic acid, 8-Benzo[1,3]dioxol-5-yl-6-benzo[1,3]dioxol-5-ylmethyl-5,5-dioxo-5,6-dihydro-1,3-dioxa5$\lambda^6$-thia-6-aza-cyclopenta[b]naphthalene-7-carboxylic acid, 2,4-Bis-benzo[1,3]dioxol-5-yl-1,1-dioxo-1,2-dihydro-1$\lambda^6$-benzo[e][1,2]thiazine-3-carboxylic acid, 2,4-Bis-benzo[1,3]dioxol-5-yl-6,7-dimethoxy-1,1-dioxo-1,2-dihydro-1$\lambda^6$-benzo[e][1,2]thiazine-3-carboxylic acid, 4-Benzo[1,3]dioxol-5-yl-2-(2-chloro-benzyl)-1,1-dioxo-1,2-dihydro-1$\lambda^6$-benzo[e][1,2]thiazine-3-carboxylic acid, 2-Benzo[1,3]dioxol-5-ylmethyl-4-(4-chloro-2,6-dimethoxy-phenyl)-1,1-dioxo-1,2-dihydro-1$\lambda^6$-benzo[e][1,2]thiazine-3-carboxylic acid, 4-(Benzo[1,3]dioxol-5-yl)-2-isobutyl-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-yl)-6-methoxy-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-yl)-7-methoxy-1,1-dioxo-1,2-dihydro-1$\lambda^6$-benzo[e][1,2]thiazine-3-carboxylic acid, 6-Benzo[1,3]dioxol-5-yl-8-(benzo[1,3]dioxol-5-yl)-5,5-dioxo-5,6-dihydro-1,3-dioxa -5$\lambda^6$thia-6-aza-cyclopenta[b]naphthalene-7-carboxylic acid, 2-Benzo[1,3]dioxol-5-ylmethyl-4-(2,3-dihydro-benzo[1,4]dioxin-6-yl)-1,1-dioxo-1,2-dihydro-1$\lambda^6$-benzo[e][1,2]thiazine-3-carboxylic acid, 4-(Benzo[1,3]dioxol-5-yl)-2-(2,3-dihydro-benzo[1,4]dioxin-6-ylmethyl)-1,1-dioxo-1,2-dihydro-1$\lambda^6$-benzo[e][1,2]thiazine-3-carboxylic acid and 4-(Benzo[1,3]dioxol-5-yl)-2-cyclohexylmethyl-1,1-dioxo-1,2-dihydro-1$\lambda^6$-benzo[e][1,2]thiazine-3-carboxylic acid.

5. A compound selected from 4-(Benzo[1,3]dioxol-5-ylsulfanyl)-2-methyl-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-ylsulfanyl)-1,1-dioxo-1,2-dihydro-1$\lambda^6$-benzo[e][1,2]thiazine-3-carboxylic acid, 4-(Benzo[1,3]dioxol-5-ylsulfanyl)-2-benzyl-1,1-dioxo-1,2-dihydro-1$\lambda^6$-benzo[e][1,2]thiazine-3-carboxylic acid, 4-(Benzo[1,3]dioxol-5-ylsulfanyl)-2-(4-methoxy-benzyl)-1,1-dioxo-1,2-dihydro-1$\lambda^6$-benzo[e][1,2]thiazine-3-carboxylic acid, 4-(Benzo[1,3]dioxol-5-ylsulfanyl)-1,1-dioxo-2-(3,4,5-trimethoxy-benzyl)-1,2-dihydro-1$\lambda^6$-benzo[e][1,2]thiazine-3-carboxylic acid, 4-(Benzo[1,3]dioxol-5-ylsulfanyl)-2-(carboxymethoxy-4-methoxy-benzyl)-1,1-dioxo-1,2-dihydro-1$\lambda^6$-benzo[e][1,2]thiazine-3-carboxylic acid, 4-(Benzo[1,3]dioxol-5-ylsulfanyl)-2-(6-chloro-benzo[1,3]dioxol-5-ylmethyl)-1,1-dioxo-1,2-dihydro-1$\lambda^6$-benzo[e][1,2]thiazine-3-carboxylic acid, 4-(Benzo[1,3]dioxol-5-ylsulfanyl)-2-(7-methoxy-benzo[1,3]dioxol-5-ylmethyl)-1,1-dioxo-1,2-dihydro-1$\lambda^6$-benzo[e][1,2]thiazine-3-carboxylic acid., 2-Benzo[1,3]dioxol-5-ylmethyl-4-(3,4-dimethoxy-phenylsulfanyl)-1,1-dioxo-1,2-dihydro-1$\lambda^6$-benzo[e][1,2]thiazine-3-carboxylic acid, 2-Benzo[1,3]dioxol-5-ylmethyl-1,1-dioxo-4-(3,4,5-trimethoxy-phenylsulfanyl)-1,2-dihydro-1$\lambda^6$-benzo[e][1,2]thiazine-3-carboxylic acid, N-(4-Benzo[1,3]dioxol-5-ylsulfanyl-2-benzo[1,3]dioxol-5-ylmethyl-1,1-dioxo-1,2-dihydro-1$\lambda^6$-benzo[e][1,2]thiazine-3-carbonyl)benzenesulfonamide., 2-Benzo[1,3]dioxol-5-ylmethyl-4-(3-methoxy-phenylsulfanyl)-1,1-dioxo-1,2-dihydro-1$\lambda^6$-benzo[e][1,2]thiazine-3-carboxylic acid, 2-Benzo[1,3]dioxol-5-ylmethyl-4-(benzo[1,3]dioxol-5-ylsulfanyl)-6,7-dimethoxy-1,1-dioxo-1,2-dihydro-1$\lambda^6$-benzo[e][1,2]thiazine-3-carboxylic acid., 2-Benzo[1,3]dioxol-5-ylmethyl-4-(benzo[1,3]dioxol-5-ylsulfanyl)-6-methoxy-1,1-dioxo-1,2-dihydro-1$\lambda^6$-benzo[e][1,2]thiazine-3-carboxylic acid, 6-Benzo[1,3]dioxol-5-ylmethyl-8-(benzo[1,3]dioxol-5-ylsulfanyl)-5,5-dioxo-5,6-dihydro-1,3-dioxa-5$\lambda^6$-thia-6-aza-cyclopenta[b]naphthalene-7-carboxylic acid, 4-(Benzo[1,3]dioxol-5-ylsulfanyl)-2-isobutyl-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfinyl)-6,7-dimethoxy-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfinyl)-6-methoxy-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfinyl)-7-methoxy-1,1-dioxo-1,2-dihydro-1$\lambda^6$-benzo[e][1,2]thiazine-3-carboxylic acid, 6-Benzo[1,3]dioxol-5-yl-8-(benzo[1,3]dioxol-5-ylsulfinyl)-5,5-dioxo-5,6-dihydro-1,3-dioxa-5$\lambda^6$thia -6-aza-cyclopenta[b]naphthalene-7-carboxylic acid, 2-Benzo[1,3]dioxol-5-ylmethyl-4-(2,3-dihydro-benzo[1,4]dioxin-6-ylsulfanyl)-1,1-dioxo-1,2-dihydro-1$\lambda^6$-benzo[e][1,2]thiazine-3-carboxylic acid, 4-(Benzo[1,3]dioxol-5-ylsulfanyl)-2-(2,3-dihydro-benzo[1,4]dioxin-6-ylmethyl)-1,1-dioxo-1,2-dihydro-1$\lambda^6$-benzo[e][1,2]thiazine-3-carboxylic acid, 4-(Benzo[1,3]dioxol-5-ylsulfanyl)-2-cyclohexylmethyl-1,1-dioxo-1,2-dihydro-1$\lambda^6$-benzo[e][1,2]thiazine-3-carboxylic acid, 2-Benzo[1,3]dioxol-5-yl-4-(benzo[1,3]dioxol-5-ylsulfanyl)-1,1-dioxo-1,2-dihydro-1$\lambda^6$-benzo[e][1,2]thiazine-3-carboxylic acid, and 2-Benzo[1,3]dioxol-5-yl-4-(benzo[1,3]dioxol-5-ylsulfanyl)-6,7-dimethoxy-1,1-dioxo-1,2-dihydro-1$\lambda^6$-benzo[e][1,2]thiazine-3-carboxylic acid, 4-(Benzo[1,3]dioxol-5-ylsulfanyl)-2-(2-chloro-benzyl)-1,1-dioxo-1,2-dihydro-1$\lambda^6$-benzo[e][1,2]thiazine-3-carboxylic acid, 2-Benzo[1,3]dioxol-5-ylmethyl-4-(4-chloro-2,6-dimethoxy-phenylsulfanyl)-1,1-dioxo-1,2-dihydro-1$\lambda^6$-benzo[e][1,2]thiazine-3-carboxylic acid and 2-(2-Benzo[1,3]dioxol-5-ylmethyl)-4-(benzo[1,3]dioxol-5-ylsufinyl)-1,1-dioxo-1,2-dihydro-1$\lambda^6$-benzo[e][1,2]thiazine-3-carboxylic acid.

6. A compound named

2-Methyl-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-1,1-dioxo-4-(trifluoro-methanesulfonyloxy)-1,2-dihydro-1$\lambda^6$-benzo[e][1,2]thiazine-3-carboxylic acid methyl ester, 2-Benzyl-1,1-dioxo-4-(trifluoro-methanesulfonyloxy)-1,2-dihydro-1$\lambda^6$-benzo[e][1,2]thiazine-3-carboxylic acid methyl ester, 2-(4-Methoxy-benzyl)-1,1-dioxo-4-(trifluoro-methanesulfonyloxy)-1,2-dihydro-1$\lambda^6$-benzo[e][1,2]thiazine-3-carboxylic acid methyl ester, 1,1-Dioxo-4-(trifluoro-methanesulfonyloxy)-2-(3,4,5-trimethoxy-benzyl)-1,2-dihydro-1$\lambda^6$-benzo[e][1,2]thiazine-3-carboxylic acid methyl ester, 2-(2-Ethoxycarbonyl-methoxy-4-methoxy-benzyl)-1,1-dioxo-4-(trifluoro-methane-sulfonyloxy)-1,2-dihydro-1$\lambda^6$-benzo[e][1,2]thiazine-3-carboxylic acid methyl ester, 2-(6-Chloro-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, 2-(7-Methoxy-benzo[1,3]dioxol-5-ylmethyl)-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6,7-dimethoxy-1,1-dioxo-4-(trifluoro-methanesulfonyloxy)-1,2-dihydro-1$\lambda^6$-benzo[e][1,2]thiazine-3-carboxylic acid methyl ester, 2-Benzo[1,3]dioxol-5-ylmethyl-6-methoxy-1,1-dioxo-4-(trifluoro-methanesulfonyloxy)-1,2-dihydro-1$\lambda^6$-benzo[e][1,2]thiazine-3-carboxylic acid methyl ester, 6-Benzo[1,3]dioxol-5-ylmethyl-5,5-dioxo-8-(trifluoro-methanesulfonyloxy)-5,6-dihydro-1,3-dioxa-5$\lambda^6$-thia- 6-aza-cyclopenta[b]naphthalene-7-carboxylic acid methyl ester, 2-Benzo[1,3]dioxol-5-ylmethyl-7-methoxy-1,1-dioxo-4-(trifluoro-methanesulfonyloxy)-1,2-dihydro-1λ⁶-benzo[e][1,2]thiazine-3-carboxylic acid methyl ester, 2-Benzo[1,3]dioxol-5-ylmethyl-6-propyloxy-1,1-dioxo-4-(trifluoro-methanesulfonyloxy)-1,2-dihydro-1λ⁶-benzo[e][1,2]thiazine-3-carboxylic acid methyl ester, 2-Benzo[1,3]dioxol-5-ylmethyl-7-propyloxy-1,1-dioxo-4-(trifluoro-methanesulfonyloxy)-1,2-dihydro-1λ⁶-benzo[e][1,2]thiazine-3-carboxylic acid methyl ester, 2-Benzo[1,3]dioxol-5-ylmethyl-7-benzyloxy-1λ⁶-methoxy-1,1-dioxo-4-(trifluoro-methane-sulfonyloxy)-1,2-dihydro-1λ⁶-benzo[e][1,2]thiazine-3-carboxylic acid methyl ester, 2-Benzo[1,3]dioxol-5-ylmethyl-6-benzyloxy-7-methoxy-1,1-dioxo-4-(trifluoro-methane-sulfonyloxy)-1,2-dihydro-1λ⁶-benzo[e][1,2]thiazine-3-carboxylic acid methyl ester, 2-Benzo[1,3]dioxol-5-ylmethyl-6,7,8-trimethoxy-1,1-dioxo-4-(trifluoro-methane- sulfonyloxy)-1,2-dihydro-1λ⁶-benzo[e][1,2]thiazine-3-carboxylic acid methyl ester, 2-Benzo[1,3]dioxol-5-ylmethyl-5,6,7,8-tetra-methoxy-1,1-dioxo-4-(trifluoro-methane-sulfonyloxy)-1,2-dihydro-1λ⁶-benzo[e][1,2]thiazine-3-carboxylic acid methyl ester, 2-Cyclohexylmethyl-1,1-dioxo-4-(trifluoro-methanesulfonyloxy)-1,2-dihydro-1λ⁶-benzo[e][1,2]thiazine-3-carboxylic acid methyl ester, 2-Cyclopentylmethyl-1,1-dioxo-4-(trifluoro-methanesulfonyloxy)-1,2-dihydro-1λ⁶-benzo[e][1,2]thiazine-3-carboxylic acid methyl ester, 2-(2-Chloro-benzyl)-1,1-dioxo-4-(trifluoro-methanesulfonyloxy)-1,2-dihydro-1λ⁶-benzo[e][1,2]thiazine-3-carboxylic acid methyl ester, 2-(2,3-Dihydro-benzo[1,4]dioxin-6-ylmethyl)-1,1-dioxo-4-(trifluoro-methanesulfonyloxy)-1,2-dihydro-1λ⁶-benzo[e][1,2]thiazine-3-carboxylic acid methyl ester, 2-Benzo[1,3]dioxol-5-yl-1,1-dioxo-4-(trifluoro-methanesulfonyloxy)-1,2-dihydro-1λ⁶-benzo[e] [1,2]thiazine-3-carboxylic acid methyl ester, 2-Benzo[1,3]dioxol-5-yl-6,7-dimethoxy-1,1-dioxo-4-(trifluoro-methanesulfonyloxy)-1,2-dihydro-1λ⁶-benzo[e] [1,2]thiazine-3-carboxylic acid methyl ester, 2-Benzo[1,3]dioxol-5-yl-6-methoxy-1,1-dioxo-4-(trifluoro-methanesulfonyloxy)-1,2-dihydro-1λ⁶-benzo[e] [1,2]thiazine-3-carboxylic acid methyl ester, 2-Benzo[1,3]dioxol-5-yl-7-methoxy-1,1-dioxo-4-(trifluoro-methanesulfonyloxy)-1,2-dihydro-1λ⁶-benzo[e] [1,2]thiazine-3-carboxylic acid methyl ester, 2-Benzo[1,3]dioxol-5-yl-6-propyloxy-1,1-dioxo-4-(trifluoro-methanesulfonyloxy)-1,2-dihydro-1λ⁶-benzo[e] [1,2]thiazine-3-carboxylic acid methyl ester, 2-Benzo[1,3]dioxol-5-yl-7-propyloxy-1,1-dioxo-4-(trifluoro-methanesulfonyloxy)-1,2-dihydro-1λ⁶-benzo[e] [1,2]thiazine-3-carboxylic acid methyl ester, 6-Benzo[1,3]dioxol-5-yl-5,5-dioxo-8-(trifluoro-methanesulfonyloxy)-5,6-dihydro-1,3-dioxa-5λ⁶-thia-6-aza-cyclopenta[b]naphthalene-7-carboxylic acid methyl ester, 2- Isobutyl-1,1-dioxo-4-(trifluoro-methane sulfonyloxy)-1,2-dihydro-1λ⁶-benzo[e][1,2]-thiazine-3-carboxylic acid methyl ester, (5,6,7-Trimethoxy-1,1,3-trioxo-1,3-dihydro-1λ⁶-benzo[d]isothiazol-2-yl)-acetic acid methyl ester, 2-Benzo[1,3]dioxol-5-yl-5,6-dimethoxy-1,1-dioxo-1,2-dihydro-1λ⁶-benzo[d]isothiazol-3-one, or 2-Benzo[1,3]dioxol-5-yl-1,1-dioxo-1,2-dihydro-1λ⁶-benzo[d]isothiazol-3-one.

7. A pharmaceutical composition comprising a therapeutically effective amount of a compound of claim 1 in admixture with a pharmaceutically acceptable carrier.

8. A method of inhibiting elevated levels of endothelin comprising administering to a host in need thereof a therapeutically effective amount of a compound of claim 1 in unit dosage form.

9. A method of treating subarachnoid hemorrhage comprising administering to a host suffering therefrom a therapeutically effective amount of a compound of claim 1 in unit dosage form.

10. A method of treating essential, renovascular, malignant and pulmonary hypertension comprising administering to a host suffering therefrom a therapeutically effective amount of a compound of claim 1 in unit dosage form.

11. A method of treating congestive heart failure comprising administering to a host suffering therefrom a therapeutically effective amount of a compound of claim 1 in unit dosage form.

12. A method of treating cerebral ischemia or cerebral infarction comprising administering to a host suffering therefrom a therapeutically effective amount of a compound of claim 1 in unit dosage form.

13. A process of the preparation of key intermediate

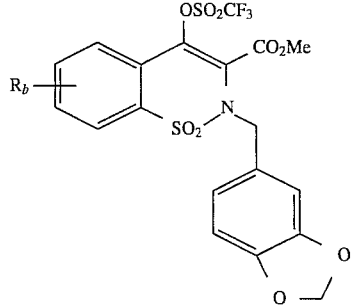

wherein $R_b$ is as defined in claim 1, which comprises treating

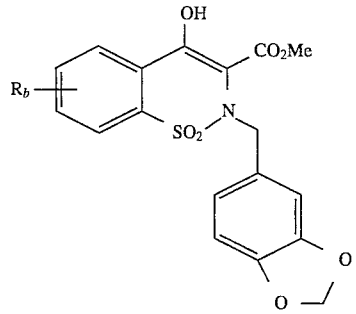

with trifluoromethanesulphonic anhydride and pyridine in methylene chloride at room temperature for about 1 hour.

14. Process for the preparation of

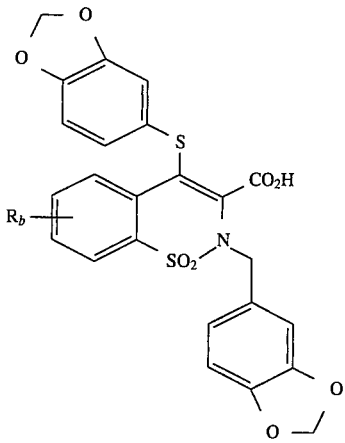

wherein $R_b$ is as defined in claim 1, which comprises adding sodium (3,4-methylenedioxy)phenyl thiolate to a solution of

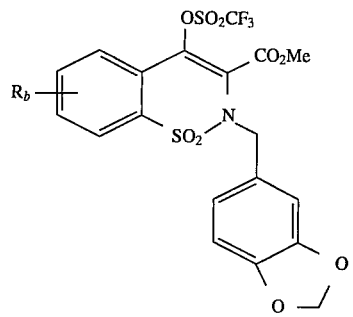

in DMF, isolating the adduct

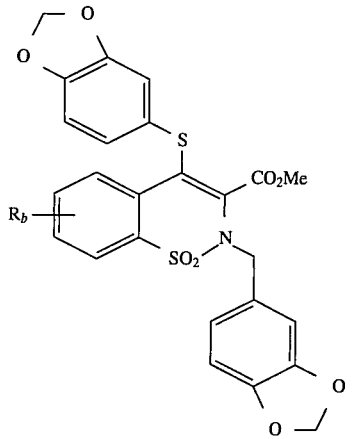

by chromatography, and saponifying it with aqueous lithium hydroxide.

15. A process for the preparation of a compound

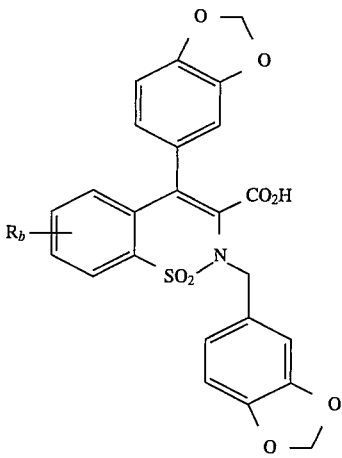

wherein $R_b$ is as defined in claim 1, which comprises coupling

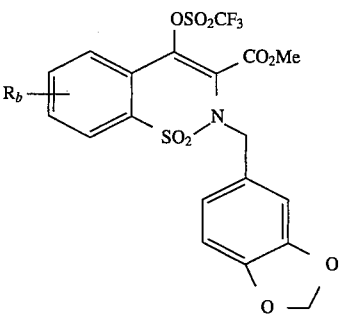

with (3,4-methylenedioxy)phenyl boronic acid mediated by palladium and isolating the adduct produced by chromatography and saponifying it with aqueous lithium hydroxide.

* * * * *